US011390844B2

(12) United States Patent
Montesinos Seguí et al.

(10) Patent No.: US 11,390,844 B2
(45) Date of Patent: Jul. 19, 2022

(54) USE OF COMPOSITIONS CONTAINING *STREPTOMYCES MELANOSPOROFACIENS* AGL225 IN CONTROLLING PLANT DISEASES

(71) Applicant: AGROLAC, S.A., Badalona (ES)

(72) Inventors: Emilio Montesinos Seguí, Banyoles (ES); Esther Badosa Romaño, Santa Pau (ES); Isabel Mora Pons, Girona (ES); Mireia Puig Garcia, Badalona (ES)

(73) Assignee: AGROLAC, S.A., Badalona (ES)

( * ) Notice: Subject to any disclaimer, the term of this patent is extended or adjusted under 35 U.S.C. 154(b) by 42 days.

(21) Appl. No.: 16/753,636

(22) PCT Filed: Oct. 5, 2018

(86) PCT No.: PCT/EP2018/077169
§ 371 (c)(1),
(2) Date: Apr. 3, 2020

(87) PCT Pub. No.: WO2019/068887
PCT Pub. Date: Apr. 11, 2019

(65) Prior Publication Data
US 2020/0267994 A1    Aug. 27, 2020

(30) Foreign Application Priority Data

Oct. 6, 2017    (EP) .................................... 17382669

(51) Int. Cl.
*C12N 1/20*      (2006.01)
*A01N 63/28*    (2020.01)
*C12R 1/465*    (2006.01)

(52) U.S. Cl.
CPC ............... *C12N 1/20* (2013.01); *A01N 63/28* (2020.01); *C12N 1/205* (2021.05); *C12R 2001/465* (2021.05)

(58) Field of Classification Search
None
See application file for complete search history.

(56) References Cited

U.S. PATENT DOCUMENTS

2007/0237755 A1    10/2007    Beaulieu et al.
2014/0057336 A1    2/2014    Tzeng et al.

FOREIGN PATENT DOCUMENTS

KR        100869668 B1    11/2008
WO    WO 2010115802 A1    10/2010

OTHER PUBLICATIONS

Beausejour et al. 2003 ("Effect of Streptomyces melanosporofaciens strain EF-76 and of chitosan on common scab of potato", Plant and Soil, vol. 256, 1, pp. 463-468) (Year: 2003).*
Beausejour et al. 2003 (Effect of Streptomyces melanosporofaciens stain EF-76 and of chitosan on common scab of potato; Plant and Soil 256:463-468 (Year: 2003).*
International Search Report and Written Opinion dated Nov. 29, 2018 for PCT Application No. PCT/EP2018/077169, 13 pages.
Aime, et al.: "Comparative analysis of PR gene expression in tomato inoculated with virulent *Fusarium oxysporum* f. sp. *Lycopersici* and the biocontrol strain F. oxysporum Fo47", Physioloigcal and Molecular Plant Pathology 2008; vol. 73 (1-3): 9-15. doi: 10.1016/j.pmpp.2008.10.001.
Beausejour, et al.: "Effect of Streptomyces Melanosporofaciens strain EF-76 and of chitosan on common scab of potato", Plant and Soil Jan. 1, 2003; vol. 256, pp. 463-468.
Bervanakis: "Detection and Expression of Biosynthetic Genes in Actinobacteria", A thesis submitted for the degree of Masters of Science, May 2008; Flinders University, 209 pages.
Bonaterra, et al.: "Osmotically induced trehalose and glycine betaine accumulation improves tolerance to desiccation, survival and efficacy of the postharvest biocontrol agent Pantoea agglomerans EPS125", FEMS Microbiology Letters 2005; vol. 250, pp. 7-15.
Boroujeni, et al.: "Enzymatic screening and random amplified polymorphic DNA fingerprinting of soil streptomyces isolated from Wayanad district in Keralda, India", Journal of Biological Sciences 2012: vol. 12, No. 1, pp. 43-50.
Cabrefiga, et al.: "Improvement of fitness and efficacy of a fire blight biocontrol agent via nutritional enhancement combined with osmoadaptation", Applied and Environmental Microbiology May 2011; vol. 77, No. 10, pp. 3174-3181.
Cabrefiga, et al.: "Improvement of a dry formulation of Pseudomonas fluorescens EPS62e for fire blight disease biocontrol by combination of culture osmoadaptation with a freeze-drying lyoprotectant", Journal of Applied Microbiology Jun. 2014; vol. 117, pp. 1122-1131, ISSN 1364-5072; doi: 10.1111/jam.12582.
Dahllof, et al.: "rpoB-based microbial community analysis avoids limitations inherent in 16S rRNA gene intraspecies heterogeneity", Applied and Environmental Microbiology Aug. 2000; vol. 66, No. 8, pp. 3376-3380.

(Continued)

*Primary Examiner* — Mary Maille Lyons
(74) *Attorney, Agent, or Firm* — Squire Patton Boggs (US) LLP

(57) ABSTRACT

The present invention refers to the strain *Streptomyces melanosporofaciens* AGL22 identified in the Spanish Type Culture Collection (CECT) as *Streptomyces melanosporofaciens* CECT9420, and the use of said strain as a pesticide in plants. Further aspects of the invention relate to suspensions and extracts of strain *S. melanosporofaciens* AGL225 and methods of preparing the same. Additional aspects relate to pesticidal compositions comprising *S. melanosporofaciens* AGL225. Finally the invention relates to a method for biological control of plant pests comprising administering to the plant strain *S. melanosporofaciens* AGL225, a composition including said strain or a cell-free extract derived from *S. melanosporofaciens* AGL225.

20 Claims, 6 Drawing Sheets

Specification includes a Sequence Listing.

(56) References Cited

OTHER PUBLICATIONS

Frandberg, et al.: "Antifungal activity of chitinolytic bacteria isolated from airtight stored cereal grain", Canadian Journal of Microbiology 1998; vol. 44, pp. 121-127.
Freeman, et al.: "An Overview of Plant Defenses Against Pathogens and Herbivores", Plant Pathology and Microbiology, The Plant Health instructor 2008; Iowa State University, DOI: 10.1094 / PHI-I-2008-0226-01.
Gharaibeh, et al.: "Genotypic and phenotypic Characteristics of antibiotic-producing Streptomyces soil Investigated by RAPD", Journal of Basic Microbiology 2003; vol. 43, No. 1., pp. 18-27, doi: 10.1002 / jobm.200390000.
Kim, et al.: "Phylogenetic analysis of the genera *Streptomyces* and *Kitasatospora* based on partial RNA polymerase (β-subunit gene (rpoB) sequences", Intenational Journal of Systematic Evolutionary Microbioly 2004; vol. 54, No. 2, pp. 593-598, doi: 10.1099 / ijs.0.02941-0.
Kong, et al.: "Generation of PCR-based DNA Fragments for Specific Detection of *Streptomyces saraceticus* N45", Proc. Natl. Sci. 2001; vol. 25, No. 2, pp. 119-127.
Kuchma, et al.: "Small-scale isolation of genomic DNA from *Streptomyces* mycelia or spores", BioTechniques 1998; vol. 24, No. 3, pp. 452-457.
Montesinos, et al.: "Pesticides, Microbial", Reference Module in Life Sciences, Encyclopedia of Microbiology 2009, Publisher: Elsevier Inc., Editors: Schaechter M, pp. 110-120.
Parente, et al.: "A comparison of methods for the measurement of bacteriocin activity", Journal of Microbiological Methods 1995; vol. 22, pp. 95-108.
Rintala, et al.: "PCR primers targeting the 16S rRNA gene for the specific detection of streptomycetes", Molecular and Cellular Probes 2001; vol. 15, No. 6, pp. 337-347, doi: 10.1006/mcpr.2001.0379.
Rodriguez-Kabana, et al.: "The determination of soil chitinase activity: Conditions for assay and ecological studies", Plant and Soil 1983; vol. 75, pp. 95-106, Ms 5424.
Sambrook, et al.: "Molecular Cloning: A Laboratory Manual", Chapter 13, "Mutagenesis", Cold Spring Harbor, 3rd Ed., 2001.
Sheperd, et al.: "Laboratory maintenance of *Streptomyces* species", Current Protocols in Microbiology 2010; Chapter 1: 1-10, Supplement 18, 10E.1.1, doi: 10.1002 / 9780471729259.mc10e01s18. Laboratory.
Skirling, et al.: "Methods for characterization of *Streptomyces* species". International Journal of Systematic Bacteriology Jul. 1966; vol. 16, No. 3, pp. 313-340.
Tamura, et al.: "MEGA6: Molecular Evolutionary Genetics Analysis Version 6.0", Brief Communication, Molecular Biology and Evolution Oct. 16, 2013; vol. 30, No. 12, pp. 2725-2729.
Williams, et al.: "DNA polymorphisms amplified by arbitrary primers are useful as genetic markers", Nucleic Acids Research 1990, vol. 18, No. 22, pp. 6531-6535.

\* cited by examiner

USE OF COMPOSITIONS CONTAINING STREPTOMYCES MELANOSPOROFACIENS AGL225 IN CONTROLLING PLANT DISEASES This application is a national phase entry under 35 U.S.C. § 371 of International Application No. PCT/EP2018/077169, filed on Oct. 5, 2018, which claims priority to EP Appl. No. EP17382669.4, filed Oct. 6, 2017. The contents of each of these applications are incorporated herein by reference in the entirety, including the specification, drawings, and the claims.

TECHNICAL FIELD

The present invention relates to the field of biopesticides, more particularly to strains of Streptomyces melanosporofaciens and their use in the biological control of plant diseases caused by bacteria, fungi and nematodes, especially in vegetable crops and fruit trees.

BACKGROUND ART

The adverse effects of the massive use of synthetic pesticides on the environment and on consumer health are well known. Due to these problems the control of plant diseases tends to the rational use of fungicides and bactericides, and to the application of less toxic products. In addition, plant protection is geared towards integrated pest management (IPM), combining different methods (physical, mechanical, chemical, biological, genetic, legal and cultural). This reorientation in the control of pests and diseases has led to a new legislative framework for the commercialization and use of plant protection products both in the member states of the European Union and in other countries. This regulation aims to reduce the use of conventional plant protection products and implement their sustainability through integrated pest and disease management, stating that phytosanitary control means should be preferably biological and physical.

In this context, biopesticides based on strains of microorganisms beneficial to plants, mainly bacteria and fungi associated with them, offer an alternative or complement to conventional synthetic pesticides. One of the main advantages of microbial pesticides is that their use allows a crop production free of residues, which is an advantage especially for its authorization in organic agricultural production. However, in comparison to chemical pesticides, a small number of microbial pesticides are now available, most of which are effective against diseases caused by fungi but not against bacterial diseases. Despite intense research in this field, most microbial strains that are active ingredients of commercial biological products, produce toxic secondary metabolites, lack adequate ecological suitability for plant colonization, show less efficacy than synthetic products, as well as some instability over time, which makes it difficult to formulate them in long lasting compositions. In addition, as the microbial pesticides are living organisms, the environmental (temperature, relative humidity, rain, etc.) and the host conditions (plant species, cultivar, phenological stage, etc.) have a strong influence on their biological activity, resulting in decreased or variable disease control efficiency, lower than with conventional chemical pesticides.

A problem with many microbial biopesticides is that they are incompatible with conventional synthetic pesticides, which limits their use in integrated pest and disease management in agriculture. For example, most active ingredients based on strains of fungi such as Trichoderma or Gliocladium antagonistic strains, are sensitive to fungicides. In this sense the bacteria have the advantage that they are insensitive to fungicides and therefore compatible with their simultaneous use.

In addition, one of the main requirements for the approval of microorganisms as biopesticides by the competent authorities is their biosafety, which is evaluated by agencies such as the Environmental Protection Agency (EPA) or the European Food Safety Authority (EFSA, Europe). Thus, certain microorganisms that have shown efficacy in controlling pests and diseases have been discarded as safe because of possible opportunistic pathogenicity for humans or animals, as in the case of certain species of Pseudomonas and Pantoea, which have been referred to in clinical cases, which is an obstacle to its use as biopesticidal agents.

In the development of a microbial biopesticide also the ability to industrialize the production of the microbial strain must be considered, as well as its formulation in order to have products with a long useful life. This is achieved mainly by powder formulations obtained by dehydration, but drying processes drastically affect the viability of microorganisms, especially of Gram negative bacteria (e.g. Pseudomonas), which are more sensitive than the Gram positive. In the case of the genus Streptomyces and Bacillus that produce spores, suitable formulations into three components (vegetative cells, spores and metabolites of fermentation) can be prepared with a high performance and fitness in the field crop environment.

In an effort to collect all the advantages described above, various strains of Streptomyces or related species have been commercially developed as biological control agents, such as Streptomyces lydicus WYEC 108 and Streptomyces K61 (Montesinos and Bonaterra, 2009). However, these strains show an activity profile focused mainly to fungal pathogens control.

Some Streptomyces strains have been disclosed, like S. melanosporofaciens EF-76 (WO2010115802) active against potato tuber diseases and several soil plant pathogens, S. yatensis CJS-24 (KR100869668) against various fungal diseases, and Streptomyces saracetius SS31 (US20140057336) with antifungal and nematicidal activity.

Consequently, there is still a need for improved bacterial strains to be used in the biological control of pests, with a wide range activity against plant pathogenic fungi, bacteria and nematodes.

SUMMARY OF INVENTION

The inventors have isolated a new strain of Streptomyces from a natural sample from the rhizosphere of a plant, which possesses characteristics that makes it highly suitable for use in biological pest control. The strain is characterized by a surprisingly broad pesticidal spectrum, being very efficient in controlling various phytopathogenic fungi and bacteria, as well as nematodes. This strain also induces plant defenses, which further increases its interest for use as biopesticide. The strain is also conveniently resistant to industrial processing, has long shell life and is resistant to environmental stress. Altogether, this strain overcomes several limitations shown by other strains described in the state of the art, as shown below.

A first aspect of the invention thus relates to a Streptomyces melanosporofaciens AGL225 strain identified in the Spanish Type Culture Collection as Streptomyces melanosporofaciens CECT9420.

The strain *S. melanosporofaciens* AGL225 of the invention was isolated from roots of a poplar tree (*Populus nigra*) in Girona and was deposited by the applicant, according to the Budapest Treaty, on Jul. 18, 2017 in the Colección Española de Cultivos Tipo (CECT), located at Universidad de Valencia, Parc Cientific Universitat de València, Catedrático Agustin Escardino, 9, 46980 Paterna (Valencia). The *S. melanosporofaciens* strain was deposited with the identification reference AGL225 and received the accession number CECT9420. In particular, this strain is characterized by showing:

(i) Antagonistic activity in vitro against phytopathogenic fungi and bacteria in a variety of culture media as ISP2 (International *Streptomyces* Project agar), AIA (actinomycete isolation agar), Benedict and SNM (nitrate and starch agar) (TABLE 1).

(ii) Antagonistic activity against the bacteria *Erwinia amylovora, Pseudomonas syringae* pv. tomato, *P. syringae* pv. actinidiae, *Xanthomonas arboricola* pv. pruni, and the fungus *Botrytis cinerea, Fusarium oxysporum* and *Stemphylium vesicarium* (TABLES 1, and 2);

(iii) Chitinolytic and nematicide activities against the model nematode *Caenorhabditis elegans* (TABLE 1, TABLE 4, FIG. 5).

(iv) Has the genes for production of antimicrobial polyketides type II (act04), but no genes for aminoglycoside antibiotics (FIG. 3).

(v) The culture medium where the strain has been grown, once free of cells (supernantant of the grown cell suspension), has a distinctive HPLC profile of active metabolites which are produced by the strain by fermentation. This metabolite profile is characteristic for the AGL225 strain and distinguishes it from other strains of *Streptomyces* (FIG. 4). These metabolites also have bactericidal, fungicidal and nematicidal activity.

(vi) Induces natural plant defenses by exerting a hypersensitivity reaction and also by inducing the defense genes in the plant (TABLE 3).

(vii) It has the ability to inhibit infections caused by the phytopathogenic bacteria *E. amylovora* in pear, *P. syringae* pv. tomato on tomato plants; *X. arboricola* pv pruni in *Prunus*; and the phytopathogenic fungi *Sclerotinia sclerotiorum* in lettuce, *F. oxysporum* f. sp. *radicis lycopersici* in tomato, and *B. cinerea* in tomato (FIG. 6).

The AGL225 strain has the great advantage of simultaneously exerting antifungal, antibacterial and nematicidal activity. Additionally, this strain induces natural defense mechanisms in plants. The existence of these four mechanisms simultaneously in a *Streptomyces* strain has the advantage of bringing together a wide range of disease control mechanisms for a single active ingredient in a plant protection product.

The high antagonistic activity of the strain of the invention against phytopathogenic agents is in part a consequence of the production of antimicrobial compounds which inhibit the growth of phytopathogenic bacteria and fungi, and also nematodes. These compounds include polyketides, chitinases and presumably other compounds with antimicrobial activity not yet known.

Many strains of *Streptomyces* (despite possessing antimicrobial biosynthesis genes as aminoglycosides or polyketides), have no significant antagonistic activity against phytopathogenic fungi and bacteria. In contrast, in TABLE 1 it can be seen that the strain *S. melanosporofaciens* AGL225 of the invention exhibits a broad spectrum of prominent antagonism against different phytopathogenic bacteria, and against different phytopathogenic fungi, and this is maintained surprisingly in four types of culture media. This shows the effectiveness of the strain of the invention in inhibiting infections caused by bacteria such as *E. amylovora* in pear plants pear, *P. syringae* pv. tomato in tomato plants and *X. arboricola* pv. pruni in *Prunus* (GF677), and of other plant pathogens (FIG. 6). In addition, surprisingly, the strain AGL225, apart from presenting polyketide biosynthesis genes (FIG. 3), produces chitinases, which are active against both fungi and nematodes. The nematicidal activity is demonstrated in an assay of *C. elegans* nematode mortality with cell-free supernatants from cultures as described in Example 6 (FIG. 5, TABLE 4).

This antimicrobial profile (antibacterial and antifungal simultaneously), it is surprising when compared with other strains of *Streptomyces* (see TABLE 1 where other *Streptomyces* strains isolated are listed). In addition, potent antimicrobial activity is complemented by its nematicidal and plant defense activity, somewhat peculiar to the strain of the invention.

The presence of the genes related to the synthesis of antimicrobial polyketides can be determined as described in Example 5. The antagonistic activity against phytopathogenic fungi and bacteria can be determined as described in Examples 2 and 3. The ability to control fungal and bacterial diseases in plants can be determined as described in Example 7.

Another striking property of the strain is that it develops a hypersensitivity reaction in tobacco plants (HR reaction) and induces the expression of genes related to defense mechanisms in tomato plants (Example 4, TABLE 3). It is known that certain microorganisms associated with plants, when applied as treatments in the rhizosphere or in the aerial part, can induce in them a defensive response against pathogens, is the so-called Induced Systemic Resistance (ISR). The ISR may be determined by the HR reaction in tobacco plants as disclosed in example 4. In other cases, components of these microorganisms or metabolites produced during their growth (fermentation metabolites) may induce a type of response called Systemic Acquired Resistance (SAR). The SAR may be determined by inducing defense genes like Harp genes or others in tomato plants as disclosed in example 4. These defense mechanisms induced in the plant confer resistance to infection by various pathogens, and even to situations of stress such as drought. There are examples of plant-associated bacteria such as *Pseudomonas, Bacillus*, etc. which induce these defenses in various plant species, but this property has not been previously demonstrated in *Streptomyces* strains.

The AGL225 strain also has the advantage that it does not produce aminoglycoside antibiotics. *Streptomyces* strains are well known producers of aminoglycoside antibiotics, which limits their use in integrated pest control, and in particular for biological pest control, because of safety concerns. AGL225 does not produce aminoglycosides, as it lacks the genes for expressing these substances. This is shown in FIG. 3. Instead, AGL225 does contain the biosynthetic pathway genes for synthesis of polyketide type II (act04) (Example 5), which entails the ability to produce antimicrobial polyketides suitable for biological pest control.

The *S. melanosporofaciens* AGL225 strain has several advantages which make it particularly suitable for use in integrated pest control. In the present invention the term "integrated pest management" has the usual meaning in the field of agronomy, where it is understood as a strategy that uses a variety of complementary methods: physical, mechanical, chemical, biological, genetic, legal and cultural aspects of pest control. It is an ecological method that aims to reduce or eliminate the use of chemical synthesis pesticides and to minimize the impact on the environment. There is also talk of ecological or biological pest control. Thus, in the present invention the terms "pest control", "biological pest control" are used interchangeably and refer to integrated pest control.

As effectively shown by the examples below, the strain of the invention is highly effective in preventing infections caused by different bacterial and fungal pathogens in horticultural plants and fruit trees. From the data shown below, it can also be concluded that this effectiveness is mainly due to its high antagonistic activity against these pathogens in aerial organs of the plants (leaves, fruits and/or flowers), as well as in the roots. This amazing ability is very important for biological pest control.

Thus, another aspect the invention relates to use of strain S. melanosporofaciens AGL225 as a pesticide in plants.

In the present invention the term "pesticide" is understood with its usual meaning in the field of agronomy as a product intended to kill, repel, regulate or disrupt the growth of living beings considered as pests. Clearly, due to the nature of the strain S. melanosporofaciens AGL225, in the present invention it is understood that "pesticide" is a biological or ecological pesticide, also called biopesticides.

In a further aspect the invention provides the use of strain S. melanosporofaciens AGL225 to control a disease caused by a bacteria, fungus or nematode in a plant. By "disease control" it is understood preventing, curing or ameliorating plant diseases caused by bacteria, fungi or nematodes. The strain achieves this effect because it prevents, diminishes or eradicates the pest which causing the disease and/or because it enhances natural defenses in the plants. In a particular embodiment, use of strain S. melanosporofaciens AGL225 is for controlling plant pests caused by bacteria, fungi or nematodes. This embodiment can also be expressed as use of the strain as a pesticide with bactericidal, fungicidal and nematicidal activity. The invention also provides a method for the biological control of plant pests comprising administering to the plant the S. melanosporofaciens AGL225 strain.

In one embodiment, the plant to be treated is a horticultural or fruit tree plant.

In view of its use as a pesticide in plants, it is important to be able to obtain sufficient quantities of viable cells from the strain and also of fermentation metabolites. As shown in Example 2 the composition shows a very high viability which is maintained during storage, even after concentration and lyophilization.

In a further aspect the present invention thus relates to a method obtaining viable cells of the S. melanosporofaciens AGL225 strain as defined in claim 1 comprising the steps of:
(i) inoculating the AGL225 strain in a suitable culture medium,
(ii) subjecting the inoculated culture medium of step (i) to conditions suitable for the growth of the strain to yield a cell suspension,
(iii) subjecting the cell suspension of step (ii) to separation to yield viable cells of S. melanosporofaciens AGL225 and a metabolite-containing supernatant,
(iv) collecting the cells of S. melanosporofaciens AGL225, and
(v) optionally subjecting the obtained cells to a dehydration process.

The strain of the invention may be inoculated into the liquid medium at a final concentration between 1 and 5%. Preferably, the culture to be inoculated is in an exponential growth phase. Cell multiplication is preferably allowed to reach final exponential phase or the start of stationary phase, achieving a cell concentration between $7 \times 10^{*8}$ and $2 \times 10^{*9}$ CFU/ml. It is well known that Streptomyces strains produce spores. This ability is convenient for formulating commercial biopesticides. Spores are highly resistant to stress conditions, which results in ease of industrial processing, long shelf live and high survival rate when applied to the plants of the products containing Streptomyces. In some embodiments of the invention, the AGL225 culture is grown to stationary phase or subjected to stress conditions in order to obtain spores. The culture can be then further processes as described below or filtered through Miracloth (Millipore) filter for separating the spores. An appropriate solution, such as Tween 20, may be then added to maintain an homogeneous spore suspension. The present invention also provides in another aspect spores of AGL225. These spores may be obtainable as explained above.

It is well known that spores form part of the life cycle of some plants and microorganisms, thus they may also be termed spore cells. Thus in the following embodiments, the term "cells" may include spore cells when conditions have been appropriate for their formation.

Suitable culture media for the growth of the strain of the invention are synthetic culture media, such as ISP2, AIA, Benedict and SNM. Suitable conditions for the growth of the strain are temperatures between 25 and 30° C., pH between 6 and 8, and concentration of oxygen between 10 and 50%. The growth of the strain of the invention is produced in solid medium or under stirring in liquid medium. Preferably, a liquid medium is used. An example of the detailed procedure for obtaining cells of the strain of the invention in liquid medium is set forth in Example 2. For the production in solid medium, strain AGL225 can be seeded in Petri dishes with ISP2 agar and incubated at 28° C. for 1-2 weeks. After subjecting the inoculated dishes to conditions suitable for the growth of the strain, for example, with conditions described above, suspensions of 40-60 ml with sterile distilled water are prepared from 3-4 culture plates.

Suitable separation techniques include centrifugation or filtration of the culture. By performing the centrifugation of the culture, for example at a minimum of 8000 rpm, cells may be separated from the culture medium (supernatant). The cells may then be used directly, resuspended to a desired density, subjected to dehydration or disrupted to obtain a cell free extract.

The cells obtained from the above method may be resuspended to a desired density, for instance $10^{*10}$ CFU/ml, in suitable solutions such as a buffer solution. In this way a cell suspension is obtained. To obtain a cell suspension, a suitable solution may also be the culture medium in which the cells have grown, i.e. the metabolite-containing supernatant resulting from the separation of step (iii) above. This may be advantageous because the supernatant contains active metabolites that are otherwise partially lost by separation. Another suitable solution for resuspending cells may be the use of fresh culture medium. The cell suspension may also be obtained directly by a method comprising steps (i) and (ii) of the method defined above, i.e. not subjecting the cell suspension obtained from step (ii) to separation. In this way the suspension contains the active metabolites secreted by the bacterial cells. The directly-obtained suspension may be concentrated by any suitable means known to the skilled person.

In another aspect of the invention it is provided a cell suspension of AGL225 cells obtainable as disclosed above and use of this cell suspension as a pesticide in plants, in particular for controlling plant pests caused by fungi, bacteria or nematodes. In a particular embodiment of the invention the cell suspension contains viable AGL225 cells, culture media and active metabolites that have been produced by the strain by fermenting the culture media. This cell suspension is particularly advantageous for formulating a suitable biopesticide. In another embodiment the cell suspension contains viable AGL225 cells, preferably at a high concentration, for example above $10^9$, resuspended in fresh culture medium. This latter cell suspension at high concentration may be also termed "inoculum" and be used for obtaining new viable cells of the strain when inoculated into a suitable culture medium.

As already mentioned, the supernatant obtained by separation of the cells from the culture media contains active metabolites with antagonistic activities. Therefore, another aspect of the invention provides a method for obtaining a AGL225 metabolite-containing supernatant comprising steps (i)-(iii) of the method for obtaining viable cells of the S. melanosporofaciens AGL225 as defined above and a further step of collecting the supernatant. Optionally, the resulting supernatant may be concentrated by any suitable means, such as evaporation or ultrafiltration. Another aspect refers to a method for obtaining a AGL225 metabolite-containing supernatant consisting of steps (i)-(iii) of the method for obtaining viable cells of the S. melanosporofaciens AGL225 as defined above, collecting the supernatant resulting from step (iii) and optionally concentrating said supernatant. Another aspect provides a AGL225 metabolite-containing supernatant obtainable by these methods, as well as use of this AGL225 metabolite-containing supernatant as a pesticide in plants, in particular for controlling plant pests caused by fungi, bacteria or nematodes.

Optionally, the AGL225 cells obtained by the methods defined above may be subjected to a dehydration process. The dehydration can be carried out by a lyophilization process, but the slurry can also be dried by fluidized bed drying, or by atomization. In this regard, another advantageous feature of the strain of the invention is that it exhibits a high resistance to the dehydration processes which are common in the production of microorganisms on an industrial scale, since it produces spores. The invention thus also provides dehydrated cells of AGL225 strain obtainable as defined herein. The dehydrated cells may of course also be used as a pesticide in plants, in particular for controlling plant pests caused by fungi, bacteria or nematodes.

The cells of S. melanosporofaciens AGL225 may be further processed to obtain a cell-free extract. Another aspect of the invention thus provides a method for obtaining a cell-free extract of S. melanosporofaciens AGL225 which comprises subjecting cells of S. melanosporofaciens AGL225 to:

(i) disrupting the cells of S. melanosporofaciens AGL225,
(ii) separating the cell free extract from the cell debris,
(iii) collecting the cell free extract, and
(iv) optionally subjecting the cell-free extract to a concentration process.

Suitable disrupting means are known by the skilled person and may include physical disruption, for example freeze-thaw or French Press, or chemical disruption, for example by addition of lysozyme. Suitable separation means have been describe above. Non-limiting examples of suitable processes for concentration are dehydration (lyophilization spray-drying), filtration, ultrafiltration, precipitation, centrifugation, and chromatography. The cell free extract may also be obtained from a cell suspension as defined above, preferably containing metabolite-containing supernatant.

Another aspect provides a cell-free extract of S. melanosporofaciens AGL225 obtainable by the process defined above, as well as use of this cell-free extract as a pesticide in plants, in particular for controlling plant pests caused by fungi, bacteria or nematodes.

The invention also relates to a method for the biological control of plant pests comprising administering to the plant the S. melanosporofaciens AGL225 cells, dehydrated AGL225 cells, a cell suspension of AGL225, a metabolite-containing AGL225 supernatant or an AGL225 cell-free extract, all as defined above.

In view of their use in pest control, pesticidal agents are usually formulated into compositions which also include additives suitable for agricultural use for which they are designed. The compositions of the invention may be solid (including, for example, dehydrated bacteria concentrate) or liquid (including concentrated suspensions of bacteria). Another aspect of the invention thus provides a composition comprising the strain S. melanosporofaciens AGL225, and one or more agriculturally acceptable compounds. "Agriculturally acceptable compounds" refer to those compounds and/or materials which are suitable and generally accepted for use in agriculture. In general such compounds should be non-toxic to humans and should preferably be environmentally friendly.

The invention also provides compositions comprising dehydrated cells, a cell suspension, a metabolite-containing supernatant, a cell-free extract as defined above, or combinations thereof, together with one or more agriculturally acceptable compounds. Herein after, the "composition of the invention" refers to any of the above mentioned compositions, all of which comprise the AGL225 strain or a product derived from the AGL225 strain.

In a particular embodiment, the composition of the invention may contain compounds for improving the adherence of the strains in the plants to be treated, phytofortifying compounds, nutrients, humectants, stabilizers, osmoprotectants, antioxidants, sunscreens, buffering compounds or combinations thereof. Some adhesion enhancing compounds are gelatins, starches, pectins, alginates and various types of gums such as xanthans. Many of these compounds are also humectants. Sunscreens include dyes such as Congo red. Phytofortifiers are compounds that may favor in crops vigor or tolerance to pathogens or adverse environmental conditions. Non-limiting examples of phytofortifiers are jasmonic acid analogues and certain defensive stimulants in plants such as harpines, chitosans, and laminarins. In particular the compositions of the invention contain at least one osmoprotector. Non-limiting examples of osmoprotective compounds are betaines, amino acids and trehalose. Improvement of the efficacy of biological control agents against infection by several phytopathogens by means of physiological adaptation (osmoprotectants) and nutritional enhancement, has been demonstrated in several microbial pesticides. For example, the survival under water stress and efficacy of disease control has been proven in Pantoea agglomerans EPS125 against post-harvest rot of fruit caused by Penicillium expansum, by amendment of the formulation with osmolytes (e.g. trehalose) (Bonaterra et al. 2005). In addition, the fitness and efficacy of control of fireblight disease of apple and pear trees has been improved in Pseudomonas fluorescens EPS62a by nutritional enhancement (e.g. adding glycine, Tween80) and osmolytes (e.g. glycine-betaine) (Cabrefiga et al. 2011, Cabrefiga et al. 2014). Interestingly, the effect of the combination of the biological control bacteria with the osmolyte and/or with the specific nutrient, provided a synergistic effect with better efficacy of control, but also more consistent between trials.

In a further aspect the present invention provides a composition comprising the AGL225 strain and at least one additional pesticide, said additional pesticide not adversely affecting the activity of strain AGL225. In one embodiment, the additional pesticide is a bactericide, a fungicide, a nematocide or an insecticide. In another embodiment, the additional pesticide is a biopesticide. In another embodiment the biopesticide is another bacterial strain with fungicidal, bactericidal and/or nematicidal activity. Preferably, the additional pesticide is *Streptomyces yatensis* AGL148.

A further aspect of the invention provides for the use of any of the compositions defined above as a pesticide in plants, in particular for controlling plant pests caused by fungi, bacteria or nematodes, as well as a method for the biological control of plant pests comprising administering to the plant any of the composition as defined above.

As with the strain *S. melanosporofaciens* AGL225, the inventors have found that the strain *S. yatensis* AGL148 shows the great advantage of simultaneously exerting antifungal, antibacterial and nematicide activity. The strain *S. yatensis* AGL148 was isolated from soil in a field of walnut trees in Girona (Spain), and was deposited by the applicant, according to the Budapest Treaty, on Jul. 18, 2017 in the Colección Española de Cultivos Tipo (CECT), located at Universidad de Valencia, Parc Cientific Universitat de València, Catedrático Agustin Escardino, 9, 46980 Paterna (Valencia). The *S. yatensis* strain was deposited with the identification reference AGL148 and received the accession number CECT9421.

This strain also induces natural defense mechanisms in plants. *S. yatensis* AGL148 differs from AGL225 in the specific antagonistic pattern but provides the same advantage of bringing together a wide range of disease control for a single active ingredient in a plant protection product. *S. yatensis* AGL148 is also safe for use in biological pest control and has properties, such as spore-forming capacity, that makes it particularly suitable for industrial biopesticide production and use.

Thus, the disclosure also refers to a *S. yatensis* AGL148 strain identified in the Spanish Type Culture Collection (CECT) as *Streptomyces yatensis* CECT9421. As illustrated in the examples below, strain AGL148 is characterized by having the following properties:

(i) Antagonistic activity against the bacteria *E. amylovora, P. syringae* pv tomato, *P. syringae* pv actinidiae, *arboricola* pv pruni X., and fungi *B. cinerea, F. oxysporum* and *S. vesicarium* (TABLE 1);

(ii) Antagonistic activity in vitro in a wide variety of culture media such as ISP2, AIA, Benedict and SNM (TABLE 1).

(iii) Chitinolytic and nematicide activity against nematode *C. elegans* (FIG. 5, TABLE 4).

(iv) Has the genes for polyketide production of antimicrobial type II (act04/ACT8), but no genes of aminoglycoside antibiotics (FIG. 3).

(v) The culture medium where the strain has been grown, once free of cells (supernatant of the grown cell suspension), has a distinctive HPLC profile of active metabolites which are produced by the strain by fermentation. This metabolite profile is characteristic for the AGL225 strain and distinguishes it from other strains of *Streptomyces* (FIG. 4). These metabolites also have bactericidal, fungicidal and nematicidal activity.

(vi) Induces natural plant defenses by exerting an hypersensitivity reaction by infiltrating cells in tobacco leaves (HR reaction) and also by inducing the defense genes Harp in tomato plants (TABLE 3).

(vii) Has the ability to inhibit infections caused by phytopathogenic bacteria *E. amylovora* in pear, *P. syringae* pv. Tomato on tomato plants; *X. arboricola* pv and. pruni in *Prunus*; and phytopathogenic fungi *S. sclerotiorum* on lettuce, *F. oxysporum* f. Sp. *radicis lycopersici* in tomato- and *B. cinerea* in tomato (FIG. 6).

All aspects and embodiments described above for the *S. melanosporofaciens* AGL225 strain also apply to the *Streptomyces yatensis* AGL148 strain. Thus the invention also provides methods for obtaining *Streptomyces yatensis* AGL148 cells (including or consisting of cells in the form of spores when conditions have been appropriate for spore formation as explained above), dehydrated AGL148 cells, a cell suspension of AGL148, a metabolite-containing AGL148 supernantant and an AGL148 cell-free extract comprising the same features as defined above. The invention also provides *Streptomyces yatensis* AGL148 cells, dehydrated AGL148 cells, a cell suspension of AGL148, a metabolite-containing AGL148 supernantant and an AGL148 cell-free extract obtainable by said methods. Compositions comprising *Streptomyces yatensis* AGL148 cells, dehydrated AGL148 cells, a cell suspension of AGL148, a metabolite-containing AGL148 supernantant, an AGL148 cell-free extract or mixtures thereof, are also provided in analogue terms as defined above. Use of the strain AGL148, its derivatives (dehydrated cells, cell suspension, metabolite-containing supernantant or cell-free extract), or compositions containing them is provided as a pesticide in plants, in particular for controlling plant pests caused by fungi, bacteria or nematodes. Finally, it is provided a method for the biological control of plant pests comprising administering to the plant the strain AGL148, its derivatives (dehydrated cells, cell suspension, metabolite-containing supernantant or cell-free extract), or compositions containing them. Particular embodiments for each of these aspects which have been described above for *S. melanosporofaciens* AGL225 also apply for the aspects related to the *Streptomyces yatensis* AGL148 strain. Also, as indicated above, the term "cells" may include or consist on spore cells when conditions have been appropriate for their formation.

The invention also refers to mutants of strain *S. melanosporofaciens* AGL225 and *Streptomyces yatensis* AGL148. The term "mutants" refer to strains obtained using as starting strain the *S. melanosporofaciens* AGL225 or *Streptomyces yatensis* AGL148 of the invention, and characterized by maintaining the properties described above. A "mutant" of the strain is also understood according to the invention as a "variant". An expert in the art will understand that using the strains of the invention as starting material it is routinely possible to obtain, for example by spontaneous mutation or directed mutagenesis, mutants that retain the characteristics and relevant advantages described herein. Methods for obtaining mutants of a given bacterial strain are known in the art. Examples can be found in (Sambrook, J. and Russell, D W "Molecular Cloning: A Laboratory Manual", Chapter 13, "Mutagenesis", Cold Spring Harbor, 3rd Ed., 2001).

Throughout the description and claims the word "comprises" and its variants are not intended to exclude other technical features, additives, components or steps. In addition, the word "comprises" includes the case "consists of". Other objects, advantages and features of the invention will be apparent to those skilled in the art in part from the description and in part from the practice of the invention.

The following examples and drawings are provided by way of illustration and are not intended to be limiting of the present invention. In addition, the present invention covers all possible combinations of particular and preferred embodiments set forth herein.

EXAMPLES

Figure 1:
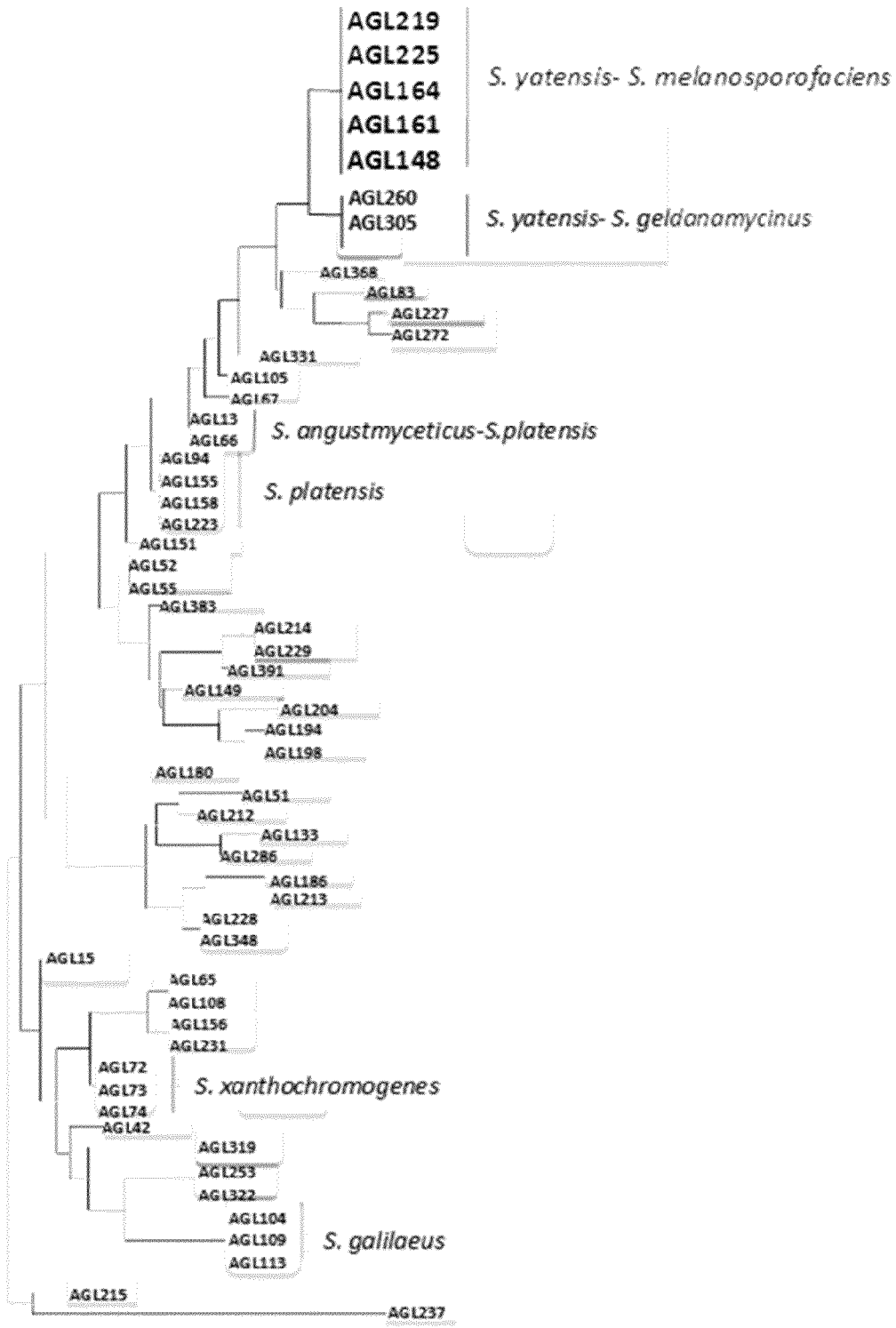
FIG. 1. Phylogenetic tree obtained using the partial sequence of rpoB and 16S rRNA genes for *Streptomyces* strains. Strains AGL225 and AGL148 appear in the upper part of the dendrogram as *S. yatensis/S. melanosporofaciens*. The dendrogam was constructed using Dice and Neighbour joining methods.

Example 1. Isolation and Characterization of the Strains *S. melanosporofaciens* AGL225 and *S. yatensis* AGL148 a) Preparation of Field Samples for Isolation of Strains of *Streptomyces*

Sampling for obtaining isolates of *Streptomyces* was conducted during the months of July to September 2014. In all 54 samples, farmland, forest areas and areas with extreme conditions (coastal dunes) were taken. Samples were processed by extraction of plant or soil materials in phosphate buffered water solution, using a homogenizer. The suspensions obtained were diluted and plated on Petri plates containing Benedict's agar, and incubated at 30° C. for 3 days. Colonies with typical morphology of *Streptomyces* were used to further obtain pure cultures. A total of 397 isolates of putative *Streptomyces* from the 54 samples were obtained. To preserve the isolates, cells and spore suspensions were obtained from pure cultures of about 5 days on solid medium by scratching the colonies and resuspension in phosphate buffer. Then, the same volume of suspension was mixed with 40% glycerol. The volume was divided in two cryotubes and after 24 h at −20° C., they were stored in a deep freezer at −70° C.

b) Identification of Isolates at the *Streptomyces* Genus Level

For confirmation that the isolates belong to the genus *Streptomyces*, a method based on PCR with primers (Strep/StrepF and StrepB/StrepE) specific to the genus was used (Rintala et al. 2001). Each suspension culture was subjected to DNA extraction using a thermal shock at 100° C. for 15 min. First PCR was performed with primers StrepB/StrepF (Forward 5'-3'ACAAGCCCTGGAAACGGGGT; SEQ ID NO: 1, Reverse 5'-3' ACGTGTGCAGCCCAAGACA; SEQ ID NO: 2), and with those strains that gave negative amplification, a new set of PCR was performed with the StrepB/StrepE primers (forward 5'-3'ACAAGCCCTG-GAAACGGGGT; SEQ ID NO: 1, Reverse 5'-3' CACCAGGAATTCCGATCT; SEQ ID NO: 3). Isolates were considered belonging to the genus *Streptomyces* if DNA amplified with either of one primers. Of the 397 isolates, 311 were finally confirmed to belong to the genus *Streptomyces*. In parallel, the colony morphology was also examined in various culture media described for *Streptomyces* (ISP2, YEMES and Oatmeal) and in potato dextrose agar (PDA) that is suitable for fungi (Shirling and Gottlieb, 1996, Scheper et al. 2010).

c) Antagonistic and Chitinolytic Activity In Vitro

Isolates obtained in pure culture, belonging to *Streptomyces* were first studied for their ability to inhibit the growth of fungi and bacteria.

Antagonism assays were performed using discs of cultures of *Streptomyces* grown for 5-7 days in ISP2 medium. These discs were placed on ISP2 agar Petri plates (or other growth media suitable for growing *Streptomyces*), which had been previously seeded with the pathogen in a confluent growth. Antagonistic activity against several plant pathogens was studied. The pathogens were selected within the plant pathogenic bacteria: *Erwinia amylovora* 6076, a mutant avirulent strain CFBP1430 (French Bacterial Collection of Plant Pathogenic Bacteria, Angers, France) that causes fire blight in Rosaceae, *Pseudomonas syringae* pv. tomato DC3000, which causes bacterial spot in tomato, *P. syringae* pv. actinidiae NCPPB3793 (National Collection of Plant Pathogenic Bacteria, United Kingdom) causing bacterial canker in kiwifruit, *Xanthomonas arboricola* pv. pruni CFBP 5563 which causes bacterial spot in stone fruit trees; and *Ralstonia solanaceum* CECT 125 (Spanish Type Culture Collection, Valencia, Spain) causing brown rot or bacterial wilt. As phytopathogenic fungi, the indicators selected were: *F. oxysporum* f.sp. *lycopersici* ATCC 201829 (American Type Culture Collection, USA) causing vascular wilting in tomato; *Botrytis cinerea* 33759B that causes gray rot in many plants, and *Stemphylium vesicarium* EPS 26 (INTEA, Agricultural Food Technology Institute, Girona) causing brown spot on pear and onion.

Once the Petri dishes were incubated at 30° C. for several days, the diameter of the growth inhibition zone around the *Streptomyces* strain and in the target microorganism was determined. An activity index taking into account the diameter of the inhibition zone was used. For bacteria the following index was used: 0, no inhibition; 1, 0 cm<I Z≤1 cm; 2, 1 cm<IZ≤2 cm; 3, 2 cm<IZ≤3 cm. For fungi the following scale: 0, no inhibition; 1, 0 cm<IZ≤0.6 cm; 2, 0.6 cm<IZ≤1.2 cm; 3, 1.2 cm<IZ≤2 cm.

Chitinolytic activity of bacterial strains was assessed using a chitin medium. A minimal culture medium consisting of mineral salts supplemented with chitin as sole nutrient was prepared (Rodriguez-Kabana et al, 1983; Frandberg and Schnürer, 1998). The culture medium contained 1.5 g/L of colloidal chitin, 2.7 g $K_2HPO_4$; 0.3 g $KH_2PO_4$, 0.7 g $MgSO_4.7H_2O$, 0.5 g NaCl, 0.13 g yeast extract and 20 g agar in 1 L of distilled water. Isolates of *Streptomyces* were picked in triplicate onto the chitin agar surface, and the plates were incubated for 7 days at 28° C. Colonies capable of secreting chitinase showed a transparent halo around them. As a positive control for chitinases we used the reference strain *Pseudomonas fluorescens* BL915. Of the 281 isolates tested, the majority (247) showed chitinase activity. Significantly, *S. melanosporofaciens* AGL225 and *S. yatensis* AGL148 were active chitinase producers, which confer these strains with potential nematicide and even insecticide activity.

Of the 311 isolates of *Streptomyces* obtained, 66 possessed antimicrobial and chitinolytic activity at different levels, and were selected for a more detailed study of antimicrobial activity. The first screening of the 66 strains selected showed different spectra and intensities of action against the eight phytopathogenic microorganisms.

As for the type of culture medium, an increased antimicrobial activity was observed in ISP2 medium against both fungi and bacteria, compared to the other media (AIA, Benedict, SNM). In one group the strains showed antibacterial activity (e.g. AGL7, AGL113, AGL15), while in the other group they showed predominantly antifungal activity (e.g. AGL148, AGL164, AGL227, AGL219). Surprisingly strain AGL225 presented antibacterial activity simultaneously with a potent antifungal activity. An example of selected strains is given in TABLE 1.

TABLE 1

Antimicrobial and chitinolytic activity of isolates of *Streptomyces* sp. against plant pathogenic bacteria (*X. arboricola* pv. *pruni*, *E. amylovora*, *P. syringae* pv. tomato, *P. syringae* pv. *actinidiae*, *Ralstonia solanacearum*); and phytopathogenic fungi (*S. vesicarium*, *F. oxysporum* and *B. cinerea*). The results shown are the average halus obtained with the growth media ISP2, AIA, Benedict and SNM. Chitinase activity is also indicated. The values correspond to the indices of activity (0 to 3 for each pathogen) that take into account the diameter of halus around the bacteria colonies or the chitin halus.

| *Streptomyces* strain | Bacteria | | | | | Fungi | | | Chitinase activity |
|---|---|---|---|---|---|---|---|---|---|
| | Xap | Ea | Pst | Psa | Rs | Sv | Fo | Bc | |
| AGL225 | 2 | 1 | 2 | 2 | 0 | 3 | 3 | 3 | 1 |
| *S. fradiae* | 2 | 1 | 2 | 2 | 2 | 2 | 3 | 3 | 0 |
| *S. hygroscopicus* | 2 | 1 | 1 | 1 | 1 | 2 | 2 | 2 | 0 |
| *S. violaceus* | 2 | 1 | 1 | 0 | 0 | 3 | 3 | 3 | 0 |
| *S. rochei* | 1 | 1 | 1 | 0 | 1 | 3 | 3 | 3 | 0 |
| *S. melanosporofaciens* | 2 | 1 | 0 | 0 | 1 | 3 | 3 | 3 | 0 |
| AGL148 | 2 | 0 | 0 | 0 | 0 | 3 | 3 | 3 | 2 |
| *S. saraceticus* Ss31 | 1 | 1 | 1 | 0 | 0 | 2 | 3 | 3 | 1 |
| AGL368 | 0 | 0 | 1 | 1 | 0 | 1 | 0 | 0 | 0 |

Xap, *Xanthomonas arboricola* pv. *pruni*;

Ea, *Erwinia amylovora*;

Pst, *Pseudomonas syringae* pv. tomato;

Psa, *P. syringae* pv. *actinidiae*;

Rs, *Ralstonia solanacearum*.

Sv, *Sthemphylium vesicarium*;

Fo, *Fusarium oxysporum*;

Bc, *Botritys cinerea*.

d) Identification of the *Streptomyces* Strains at Species Level

Of the 311 isolates originally classified as *Streptomyces*, we selected 66 with significant antimicrobial activity. The isolates were submitted to partial sequencing of the 16S rDNA and rpoB genes (Ki et al. "Structure of a protein-DNA complex essential for DNA spores of *Bacillus* protection in species', 2009, Proceedings of the National Academy of Sciences of the United States of America of the United States of America of the United States of America, Vol. 105, pp. 2806-2811). PCR was performed on DNA from the cultures with primers StrepB/StrepF, that amplify a fragment of 519 bp of 16S rDNA (Rintala et al. 2001) and with SRPOF1 primers (5'-TCGACCACTTCGGCAACCGC-3'; SEQ ID NO: 4) and SRPOR1 (5'-TCGATCGGGCA-CATGCGGCC-3'; SEQ ID NO: 5) that produces a 352 bp amplicon (Kim et al. 2001).

Amplification of the two genes was performed in an end volume of 25 ul, containing a concentration of 1× buffer, 3 mM magnesium chloride, 200 uM dNTPs, 0.2 uM of each primer, 2 U of Taq polimerase (Biootols, Spain) and 2 ul of sample. The thermocycler program consisted of 1 cycle of 95° C. for 5 min, 30 cycles of 95° C. for 45 s, 60° C. for 40 s and 2 min at 72° C.; finally at 72° C. for amplification 10 min and at the end a maintenance at 4° C. Professional TRIO thermocycler from Biometra (Biometra) was used. Once completed amplification the results were viewed in an agarose gel 1%, subjected to an electric field of 75 V for 40 min, and stained with Ethidium Bromide for 20 min. The images were captured with Molecular Imager ChemiDoc XRS+(BioRad Laboratories).

The PCR products were purified (Qiagen Kit Quiquick purification PCR), DNA concentration adjusted at 50 ng/microliter, and sequencing was performed with 5 ul of DNA and 5 ul of primers at 5 uM using a sequencer ABI PRISM™ 310 Genetic Analyzer (PE Applied Biosystems, CA, USA). Sequencing was performed in both directions of the DNA strand. The edited sequences were obtained with Chromas 2.4 (program http://downloads.informer.com/chromas/2.4/) and were analyzed and aligned using the program BioEdit Sequencing Editor (http://www.mbio.ncsu.edu/BioEdit/bioedit.html), and homology determined by the BLAST program at the NCBI database https://blast.ncbi.nlm.nih.gov/Blast.cgi).

The sequence analysis of 16S rDNA with the BLAST program (GenBank) did not allow to clearly distinguish all isolates at the species level. For this reason we proceeded to further sequencing of the gene of the beta subunit of RNA polymerase (rpoB) (Kim et al. 2004), which can be applied to strains of *Streptomyces*, and is also suitable for phylogenetic analysis (Dahllof et al. 2000; Kim et al, 2004).

Of the 66 strains, 25 matches were obtained with the GenBank database. In 9 of the 25 strains there was agreement between the two identification systems (16S rDNA and rpoB). Among the isolates belonging to *Streptomyces*, it was confirmed that the most actively antimicrobial strains pertained to *S. yatensis* (AGL148, AGL164 and AGL219) or *S. melanosporofaciens* (AGL171 and AGL225). The sequences of the strains of *S. melanosporofaciens* AGL225 and *S. yatensis* AGL148, were deposited in the GenBank (strain AGL225: gene 16S rDNA accession No. MG008625, gene rpoB accession No. MG007902; strain AGL148: gene 16S rDNA accession No. MG008626, gene rpoB accession No. MG007903).

Furthermore, a phylogenetic tree was performed with the sequences of the 16S rDNA and rpoB genes. First, they were aligned with the CLUSTALW program (http://www.ebi.ac.uk/Tools/msa/clustalo/) in order to choose the appropriate fragment length for analysis. The dendrogram was performed with the Neighbor-joining method with a 1000 bootstrap replicates using the MEGA6 (Tamura K, et al. 2013).

The phylogenetic analysis showed that most strains were distributed throughout the dendrogram, but there was a distinct very homogeneous and well defined group consisting of AGL219, AGL225, AGL164, AGL161 and AGL148 (FIG. 1). According to the homology with the GenBank data base, strain AGL148 correspond to the species *S. yatensis* and strain AGL225 to *S. melanosporofaciens*.

e) Differentiation of the *Streptomyces* Isolates at Strain Level

In order to differentiate strains of *Streptomyces* AGL225 and AGL148 from other strains of *Streptomyces*, we proceeded to determine their DNA fingerprinting profile. We used the RAPD technique (Random Amplification of Polymorphic DNA), with single short arbitrary primers (8-12 nucleotides) generated by PCR amplifications which allow typification of strains (Williams et al., 1990). A set of 25 strains from field samples and nine reference strains were used, including *S. saraceticus* SS31.

Strains were grown in ISP2 liquid medium for 5 days, and DNA was extracted using the QIAamp DNA extraction mini kit following the manufacturer's instructions.

To perform the RAPD's, the DNA of the strains (25 ng/µl) was submitted to amplification with 12 primers in a first test: LIT (5'-3'(TGCCGAGCTG; SEQ ID NO: 6, OPA9 (5'-3' GGGTAACGCC; SEQ ID NO: 7), OPA10 (5 GTTGGCGGGTGTCGGGCTGGCTT; SEQ ID NO: 8), OPA2 5'-3) (Kong et al., 2001)"-3' GTGATCGCAG; SEQ ID NO: 9) (Gharaibeh et al., 2003), OPA B9 (5'-3'GGGCGACTAC; SEQ ID NO: 10) (Boroujeni et al. 2012), d8635 (5'-3' GAGCGGCCAAAGGGAGCAGAC; SEQ ID NO: 11) (Kutchma et al., 1998), Gene 1.80.5 (5'-3'ACCCCAGCCG; SEQ ID NO: 12), Gene 1.80.7 (5'-3' GCACGCCGGA; SEQ ID NO: 13), Gene 2.80.11 (5'-3'GCAGCAGCCG; SEQ ID NO: 14), Gene 4.80.35 (5'-3' CACCTGCCGC; SEQ ID NO: 15), Gene 4.80.36 (5'-3'GGCCTCCACG; SEQ ID NO: 16), Gene 4.80.37 (5'-3' CGCCAGGAGC; SEQ ID NO: 17) (Martin et al, 2000). The best results were provided with primers LIT, d8635 and 1.80.7 allowing a greater number of bands.

The PCR cocktail was of 25 µl, 2 µl of which were the DNA of the strain. The final concentration of the buffer was 1×, the $MgCl_2$ 2.5 mM, 2 mM dNTPs, 0.4 uM primer and 1 unit Taq polymerase. A program with a sequence of two different amplification cycles (5 cycles at 37° C. and 30 cycles at 55° C.) was used. Professional TRIO thermocycler from Biometra (Biometra) was used. Once completed amplification, results were viewed on agarose gel 1.5%, that was subjected to an electric field of 75 V for 60 min, and stained with EtBr for 20 min. The results were captured with Molecular Imager ChemiDoc XRS+(BioRad Laboratories). The images of the gels, were processed with the Image Lab v.4 (Bi-Rad) program to calculate the fragment size (bp). With the data of the three primers a binary matrix was constructed to determine the presence or absence of a fragment of a particular molecular weight in strains. The calculation of the similarity was performed using the Dice coefficient and finally the dendrogram was performed with a cluster analysis using the UPGMA method (Unweighted Pair Group Method With Arithmetic Mean) with the program NTSYSpc v2.0.

Figure 2:
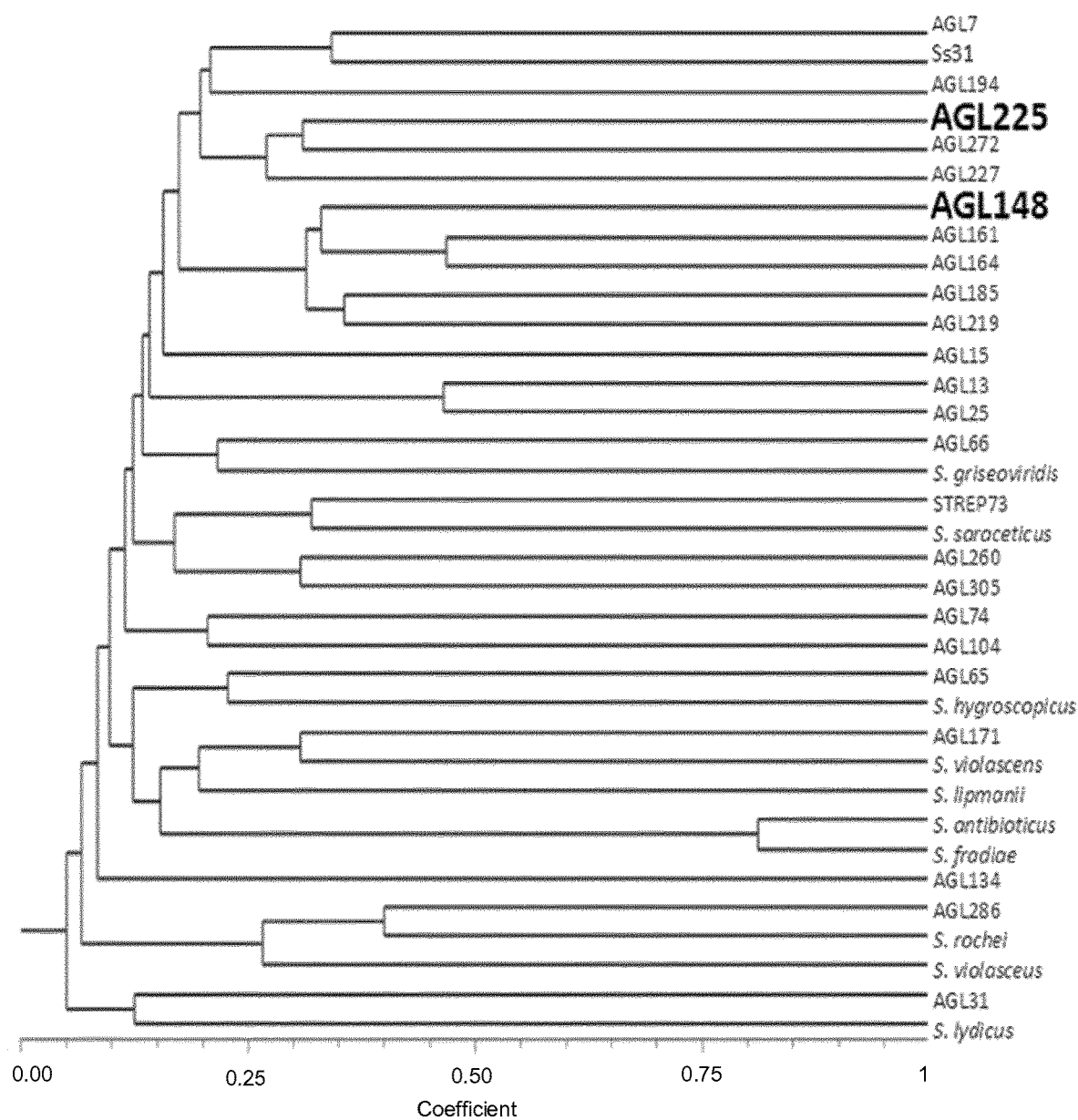
FIG. 2. Dendrogram obtained with the RAPD patterns for *Streptomyces* isolates. The distance matrix was calculated using Dice coefficient and the UPGMA grouping. Data are combined for each strain using RAPD patterns obtained with LTI, d8635 and 1.80.7 primers. Strains shown include 25 isolates of *Streptomyces* obtained in this work and nine strains from reference collections (*S. saraceticus, S. hygroscopicus, S. griseoviridis, S. violascens, S. lipmanii, S. antibioticus, S. fradiae, S. rochei* and *S. violasceus*). Strains AGL225 and AGL148 are indicated.

FIG. 2 shows the dendrogram obtained with the UPGMA method derived from the combination of RAPD patterns with LIT, d8635 and 1.80.7 primers, for the 25 isolates and ten reference strains of the species *S. saraceticus*, *S. hygroscopicus*, *S. griseoviridis*, *S. violascens*, *S. lipmanii*, *S. antibioticus*, *S. fradiae*, *S. rochei* and *S. violasceus*. It can be seen that each of the strain can be distinguished with RAPD DNA fingerprinting, particularly strains AGL225 and AGL148. Thus, the strains of the invention have a unique and distinctive RAPD pattern different from other isolates, including the ones from collections or from commercial products.

Example 2. Preparation of Cultures of the Strains of the Invention and of Cell Free Extracts, for Obtaining Concentrates of Cellular Suspensions and Extracts from the Culture Medium For the production of cells or metabolites of AGL225 and AGL148 strains, cultures were grown in ISP2 plates. To obtain a concentrated cell suspension or cell-free supernatant of cultures containing the fermentation metabolites of the *Streptomyces* of the invention, strains were cultured for 1 week in liquid ISP2 medium and incubated at 28° C. with shaking at 150 rpm. The material obtained in stationary phase was subjected to centrifugation at 8000 rpm for 15 min. The pellet containing cells can be resuspended in a small volume of phosphate buffer to obtain a concentrated cell suspension of $10^{*9}$ CFU/ml. The concentrated cell suspension can be used in further assays, like disease control in plants artificially infected with phytopathogens.

The supernatant from centrifugation, containing metabolites produced by culturing the strain, was used for antimicrobial activity assays. The supernatants were filtered through 0.45 micrometer pore filters and the filtrates were frozen at −80° C. for later use. These extracts were additionally concentrated by lyophilization to obtain a solid extract, which may be stored until use. In this case, the solid material is suspended in distilled water or methanol, or can be submitted to an extraction/partial purification of its components by phase extraction with ethyl acetate or hexane/chloroform. Such fractions may be evaporated and the pellet resuspended in methanol. All these materials can be used in antimicrobial or nematicidal activity assays, and for HPLC chromatography analysis of the active components.

Example 3. Antimicrobial Activity of Cell-Free Culture Supernatants

The culture supernatants were assayed by the Bioscreen system (Labsystems) using 100 microwell plates. Each well of the plate contained 100 ul of supernatant (direct or at the desired dilution), 80 of Luria Bertani broth (2×) and 20 ul of a suspension of *X. arboricola* pv. pruni or spores of *F. oxysporum*. The results of inhibition were transformed into arbitrary units as AU ml$^{-1}$. The AU were calculated as the inverse of the highest dilution that inhibited the growth of the pathogen (D) and multiplied by 40 (Parente et al. 1995). Table 2 shows the results of the six best strains. The supernatants of AGL13, AGL25, and AGL31 strains had antifungal activity against *F. oxysporum*, and the strain AGL286 has antibacterial activity. However, the supernatants of AGL148 and AGL225 strains were simultaneously antibacterial and antifungal.

TABLE 2

In vitro antimicrobial activity (AU ml$^{-1}$) against two pathogens of the culture supernatants of *Streptomyces* strains.

| *Streptomyces* | *X. arboricola* pv. *pruni* | *F. oxysporum* |
|---|---|---|
| AGL13 | 0 | 640 |
| AGL25 | 0 | 2560 |
| AGL31 | 0 | 1280 |
| AGL286 | 1280 | 0 |
| AGL148 | 160 | 2560 |
| AGL225 | 160 | 1280 |

Example 4. Induction of Plant Defenses a) Hypersensitive Response in Tobacco Plants (HR)

To demonstrate the ability to induce defense in plants a technique consisting of infiltrating leaves of tobacco plants was used. This method measures the hypersensitive response (HR) in a plant indicator against cells or extracts (Freeman and Beattie, 2008). Suspensions of 39 selected *Streptomyces* strains were infiltrated in the mesophyll of leaves of tobacco (*Nicotiana tabacum*). For the infiltration, a puncture was made in the reverse of the leave with the aid of a hypodermic needle. Infiltrations were performed in four different plants with a needleless syringe charged with the *Streptomyces* strain material. The plant pathogenic bacterium *Pseudomonas syringae* EPS94 at $10^8$ cfu/ml, was used as positive control, and water as a negative control. After 24-72 h of incubation of the plants symptoms were observed. The HR response consisted of blocking necrosis limited between two ribs and a light brown desiccated tissue. Of the 39 strains tested 10 strains from the collection were positive (AGL31, AGL214, AGL225, AGL227, AGL260, AGL272, AGL305, AGL148, AGL161, AGL164, AGL171, AGL174, AGL186), particularly *S. yatensis* AGL 148 and *S. melanosporofaciens* AGL 225. This result indicates their capacity to induce defense on plants according to the HR reaction in tobacco leaves.

b) Induction of the Expression of Genes Related to Defense or Stress on Plants

To confirm that the observed HR reaction in tobacco plant leaves with the treatment with AGL225 and AGL148 strains was due to the induction of genes related to the defensive response in the plant, a transcriptomic study was performed, in this case on tomato plants. Tomato was used as a model plant because of the abundant number of studies available on gene expression.

Tomato plants were grown in hydroponics, in inert substrate rockwool (Grodan© Plugs). After 2-3 weeks (phenological stage of two cotyledons) seedlings were transplanted in rockwool blocks (Grodan© Delta). These were acclimatized in the greenhouse approximately 8 weeks before conducting the tests. A single treatment with the *Streptomyces* strains was performed and samples of plant material (leaves) were taken at 24 hours to proceed to the extraction of mRNA. Reference treatment with benzothiadiazole (Bion, Syngenta), that stimulate plant defenses was used as positive control. The experimental design consisted of 9 plants per treatment (3 replicates of three plants each). For the extraction of RNA from the samples, three young leaves of three single plants (about 30 mg) were mixed and frozen with liquid nitrogen with two balls (4 mm diameter borosilicate) and stored at −70° C. The samples were homogenized with TissueLyser II (Qiagen) using a frequency of 30 Hz for 10 s. mRNA extraction was performed using Trizol reagent (Invitrogen). Quantification of the obtained RNA was done with Nanodrop system (NanoDrop quantitated© ND-1000, NanoDrop Technologies). To remove traces of DNA, samples were treated with DNase (Ambion® TURBO DNA-Free™. Live Technologies). Subsequently, the reverse transcription of the nucleic acid extracts of the samples (conversion of mRNA to cDNA) was performed with cDNA reverse transcription KITS (Invitrogen) following the manufacturer's instructions. Finally, qPCR were performed for both, the endogenous reference gene Actin (F 5'-3 CACTGTATGCCAGTGGTCGT, SEQ ID NO 18; R 5'-3': GACGGAGAATGGCATGTGGA, SEQ ID NO: 19), as well as for each of the genes of pathogenesis related proteins: PR1a (F 5'-3': TCTTGTGAGGCCCAAAATTC, SEQ ID NO: 20; R 5'-3 ATAGTCTGGCCTCTCGGACA, SEQ ID NO: 21) (Aime et al 2008), Glucanases: GluA (F 5'-3': TCTTGTGAGGCCCAAAATTC, SEQ ID NO: 22; R 5'-3': ATAGTCTGGCCTCTCGGACA, SEQ ID NO: 23) (Aime et al 2008), GLUB (F 5'-3 TTGTCGCCACCAACATT-CACA, SEQ ID NO: 24; R 5'-3': ACCATCTCGCGTGTTC-CATC, SEQ ID NO: 25), chitinases: chia (F 5'-3 TTCGGCACTGATGGAAGTGG, SEQ ID NO: 26; R 5'-3': TTTTAAGCTTGCTACACGCGG, SEQ ID NO: 27), PERAJ (F 5'-3 AGGCCCATTTTATCCGGTGG, SEQ ID NO: 28; R 5'-3': GCTAAGGCCACGTCTAGCAA, SEQ ID NO: 29), PER1 (F 5'3': TCTTAGCTGTTGCAGCTCGT, SEQ ID NO: 30; R 5'-3': CTAGTGTATGGCCACCGGAC, SEQ ID NO: 31), HARP (F 5'-3': ATTATGGCCCGTCCAT-TCCG, SEQ ID NO: 32; R 5'-3 ATGCAATGACTCCGAGGACG, SEQ ID NO: 33).

In TABLE 3 it is shown the effect of treatments on the gene expression levels (mRNA) corresponding to four genes related to defense response in plants. It was compared the effect of AGL148 and AGL225 strains, in relation to a positive control (Bion from Syngenta) and to a negative control (water). Compared to the negative control, the strain AGL148 induces expression of genes Per AJ, Pr 1a, Chia A and Harp, while the strain AGL225 induced Harp gene. The Bion positive control induces PR1a, Chia and Harp. Therefore it can be concluded that both strains induce plant defenses, but the effect is more extensive and strong in AGL148 than in AGL225.

TABLE 3

Effect of treatment of tomato plants with strains AGL225 and AGL148 in the expression levels (mRNA) of the genes, Pr 1a, Chi A, Per AJ, and Harp related to defensive response. Positive Control (Bion) and negative (water) control.

| Treatment | HR | PR1a | ChiA | PerAJ | Harp |
|---|---|---|---|---|---|
| NTC | − | 1.05 ± 0.14 | 1.17 ± 0.29 | 1.48 ± 0.50 | 1.52 ± 0.61 |
| Bion | − | >40 | 8.54 ± 4.00 | 0.34 ± 0.16 | 13.52 ± 2.02 |
| AGL148 | + | 22.23 ± 4.92 | 3.74 ± 0.42 | 1.92 ± 0.89 | 13.41 ± 2.82 |
| AGL225 | + | 0.39 ± 0.20 | 1.05 ± 0.42 | 0.19 ± 0.072 | 3.01 ± 0.59 |

PR1a, Pathogenesis-related protein;
ChiA, Chitinase;
Per AJ, Peroxidase;
Harp, Harpin-like induced protein.

Example 5. Genes and Metabolites Involved in Activity of Strains

The production of fermentation metabolites by cultures of *Streptomyces* was studied because it has been associated with the biological control activity in several microbial biopesticides (Montesinos and Bonaterra 2009). In the genus *Streptomyces* the production of numerous antimicrobial compounds from the group of aminoglycosides and polyketides, have been described. The genus *Streptomyces* is remarkable for production of secondary metabolites that give their members a wide range of applications in the phytosanitary field.

a) Characterization of Genes Involved in the Synthesis of Antimicrobial Metabolites To confirm the production of plant beneficial antimicrobial metabolites by the strains, a molecular approach was performed prior to the chemical analysis of specific metabolite profiles. We proceeded to detect genes related to the synthesis of three groups of bioactive secondary metabolites produced by actinomycetes. Three pairs of primers for biosynthesis of metabolites were used in order to detect aminoglycosides (strD01f 5'-3': CTTCGC-CATGTATCTCGGCGACAA, SEQ ID NO: 34; strD01r 5'-3': TGCCGGTGTCCTTCCAGTAG, SEQ ID NO: 35), type II polyketides (act04f 5'-3': GATGGTCTC-CACCGGCTGC, SEQ ID NO: 36; act06r 5'-3': GTCTCGTGGCGGTCGTTCTGC, SEQ ID NO: 37) and beta-lactams (pcb03f 5'-3 CGAGTCCTGGTGCTACCT-GAACC, SEQ ID NO: 38; pcb03r 5'-3': TCATCGACACGTCCAGGTGGTC, SEQ ID NO: 39) (Bervanakis, 2008). The DNA from the cultures was extracted following the same protocol as for the identification of isolates, and as described in Example 1, paragraph b). Amplification was performed in a cocktail with a volume of 25 ul, with an end concentration of 1× buffer, 3 mM magnesium chloride, 200 uM dNTPs, 0.2 uM of each first, 2 U Taq polimerase (Biootols, Spain) and 2.5 ul of sample. The thermocycler program consisted of 1 cycle of 95° C. for 5 min, 30 cycles of 95° C. for 45 s, 65° C. for 45 s and 1 min at 72° C.; finally at 72° C. for amplification 10 min and a final stage of maintenance at 4° C. Professional TRIO thermocycler from Biometra (Biometra) was used. The amplicons were separated by electrophoresis in 1.5% agarose gels in an electric field of 90 V for 40 min. Then, gels were stained with EtBr for 20 min. The results were captured with Molecular Imager ChemiDoc XRS+(BioRad Laboratories). *Streptomyces griseus* DSM40236 was used as positive check for the presence of aminoglycosides biosynthetic genes; *S. cattleya* DMS46488 (NRRL8057)) for beta-lactams and *S. nogalater* DSM40546 for polyketides.

Figure 3:
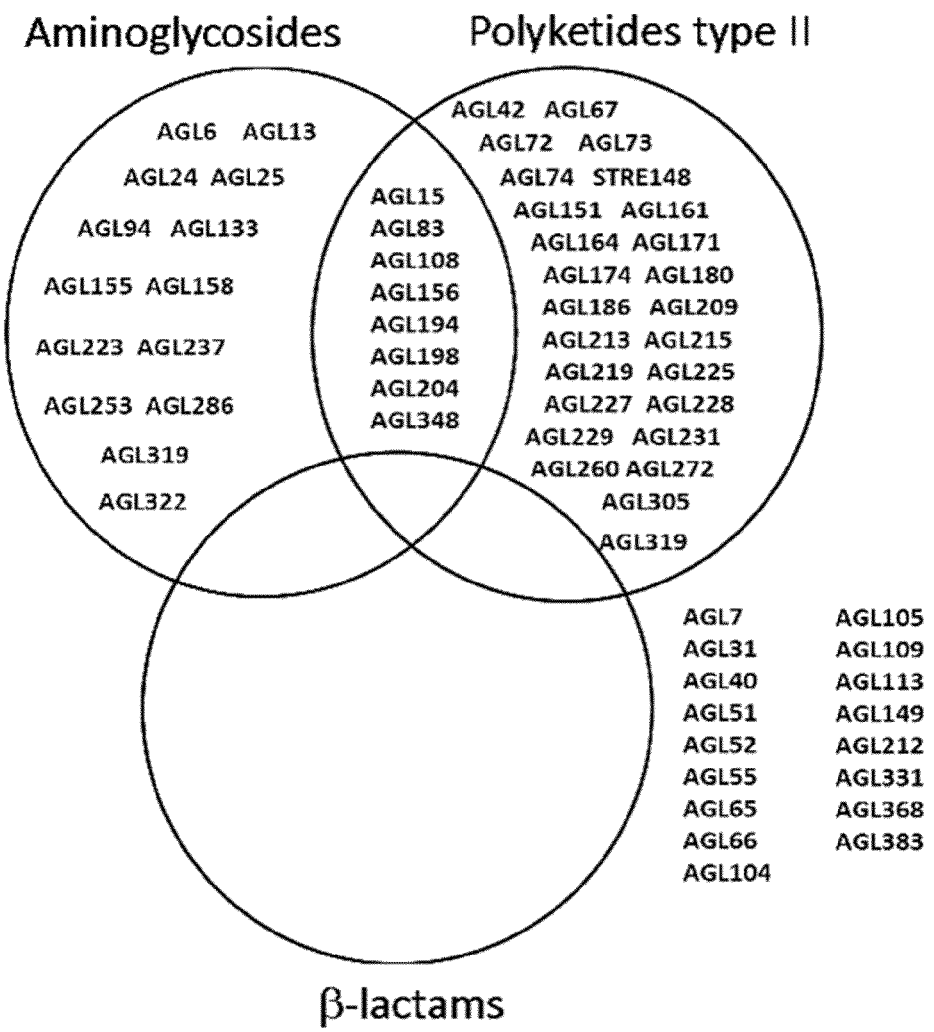
FIG. 3. Presence of the biosynthetic pathway genes of different types of metabolites (aminoglycosides, polyketides and beta-lactams) in strains of *Streptomyces* sp. The detection was performed by PCR amplification. Strains outside the circles are strains in which no amplification product was found with any of the primers for the three pathway genes.

FIG. 3 shows that of the 59 strains of the collection analyzed, 14 showed aminoglycoside biosynthesis genes, 26 strains polyketide synthesis genes, while eight strains possessed both groups of genes. None of the strains showed genes for the synthesis of beta-lactams, and 17 strains did not show any of the genes. Strains AGL225 and AGL148 were only positive for genes of type II polyketides.

b) Fermentation Metabolite Profiles

After the analysis of the three types of antimicrobial metabolite related genes, we proceeded to determine the profiles of metabolites produced by the strains by high performance liquid chromatography (HPLC). Metabolites produced in liquid culture were determined as characteristic profiles for each strain. This was made specifically for AGL225 and AGL148 strains. ISP2 culture medium was inoculated with the strains, cultured for one week at 28° C. under stirring at 150 rpm. Cultures were filtered and the supernatants frozen at −80° C. The same procedure was performed with the ISP2 uninoculated medium to be used as control.

Extraction of metabolites was performed on the culture supernatants. The extraction process consisted of hexane (1:1) and ethyl acetate (1:1), followed by evaporation and acetonitrile resuspension. 50 ul of each extract were analyzed under the following conditions: Flow rate: 1.25 ml/min; Solvents: A: Water+0.1% TFA B: acetonitrile+0.1% TFA. The chromatograms were run at 220 nm (peptide compounds), 254 nm (aromatic compounds), 280 nm (phenolic compounds). The use of C18-XF and PFP columns make possible to detect in the chromatograms at various wavelengths (220, 245 and 280 nm) differential and identificative peaks between strain AGL148 and AGL225, which conform to the several metabolites produced.

Figure 4:
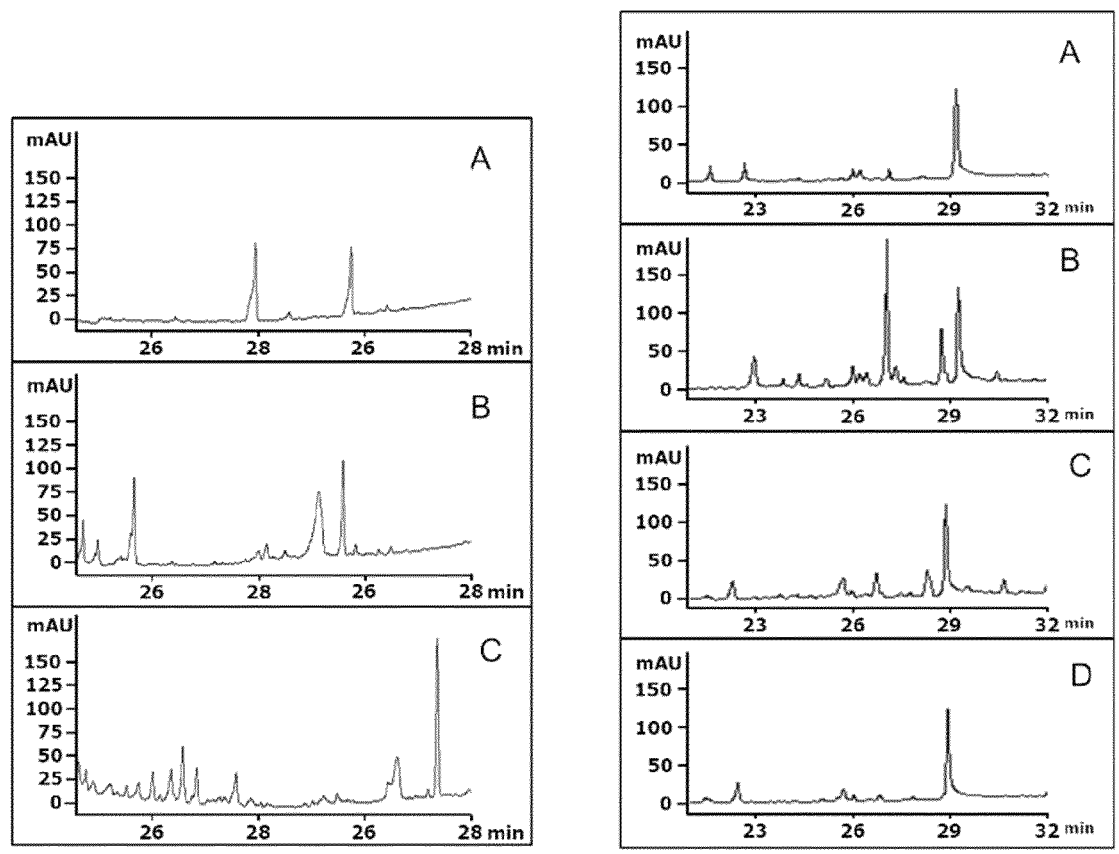
FIG. 4. Chromatographic profiles (HPLC) of *Streptomyces* strains in a C18 column Kinetex 250 (left panel) or in a C18-XB column (right panel). Left panel: ISP2 fresh culture medium (A), extract of the strain *S. yatensis* AGL148 (B) and extract of the strain *S. melanosporofaciens* AGL225 (C). Right panel: in ISP2 fresh culture medium (A), extract of the strain *S. yatensis* AGL148 (B) and extract of the strain *S. melanosporofaciens* AGL225 (C) compared with the strain *Streptomyces* sp. AGL260 (D). The Y axis shows the absorbance of each of the collected fractions (mAU=milli-absorbance units), and the x axis is the time of elution (in min).

Several profiles can be seen in FIG. 4, that show differential peaks with respect to medium components, which are produced by S. melanosporofaciens AGL225 and S. yatensis AGL148. These profiles are characteristic of such strains and are distinctive molecular fingerprints, which differ from other strains of Streptomyces. The nature of the compounds is unknown but probably were polyketide gene products, in agreement with the genes of these pathways detected by PCR.

Example 6. Nematicidal Activity

To determine the nematicidal activity of the strains, the nematode Caenorhabditis elegans WT Bristol N2 was used as a model nematode, which is a wild strain from the Caenorhabditis Genetic Center (CGC). The nematodes were grown fed on E. coli OP50 routinely. The nematode heterogeneous population resulting was treated with sodium hypochlorite (1.5%) to preserve only eggs and eliminate individuals. After several washes with M9 buffer we proceeded to the hatching of eggs, which were transferred to medium NMG with E. coli OP50 as food, and incubated until the L2 stage. At this stage, survival assays on solid and in liquid media were made. In tests on solid medium the corresponding strain of Streptomyces was seeded in NMG, instead of E. coli OP50. After 12 days of growth the L2 stage nematodes were deposited. As positive controls (pathogen controls) S. enterica subsp. enterica strain ATCC14028 (CECT4594) and LT2 (CECT4085) were used. In the liquid medium the culture supernatant of the Streptomyces strains, obtained by centrifugation as described above was tested in microplates. The test consisted of depositing 1 ml of culture supernatant and 30 microliters of NMG with a suspension of nematodes (75-100 Individuals) in each microplate well. Fresh NMG, ISP2 media and M9 buffer were used as negative controls, and the biocide sodium azide was used as nematicide control. The plates were incubated at 23° C. and individuals surviving 24 and 48 h were determined. A stereomicroscope (SMZ NIKON 1000) was used for viewing nematodes. The length and shape of nematodes was measured, and dead nematodes appeared with straight morphology, while sinusoidal and mobile individuals were considered alive.

Figure 5:
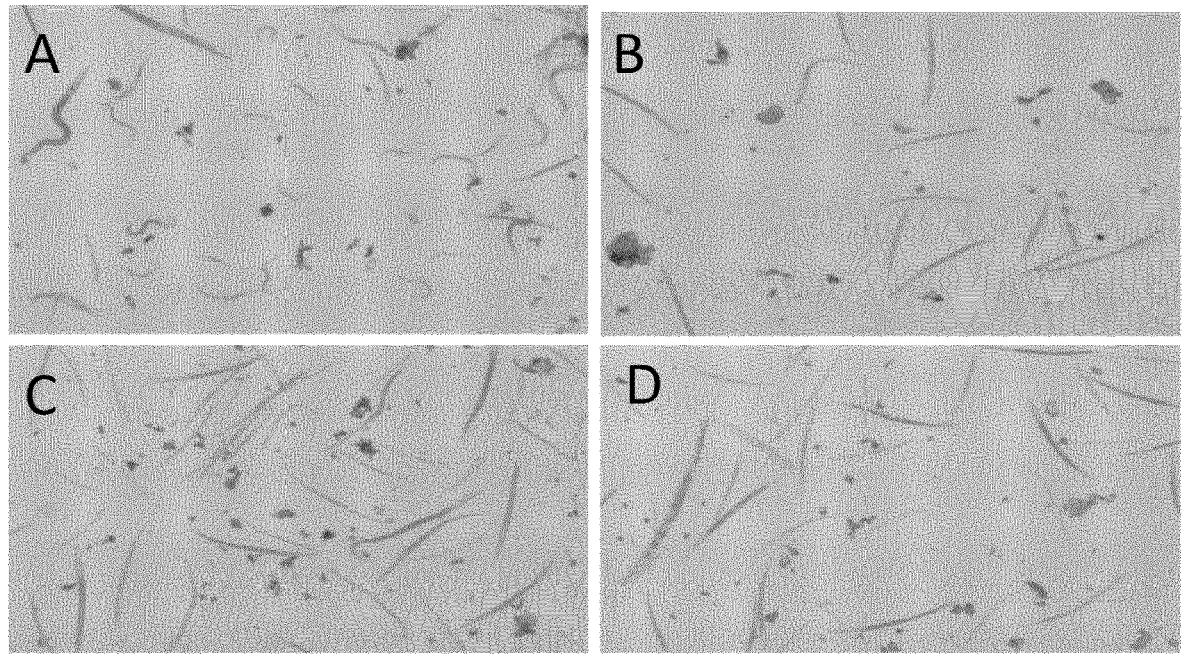
FIG. 5. Nematicidal activity on *Caenorhabditis elegans*, following treatment with supernatants from cultures of strains of *Streptomyces* in ISP2 medium. M9 buffer control with *E. coli* OP50 (A), sodium azide (B, control of mortality), supernatants of AGL148 (C) and AGL225 (D). Notice that straight nematodes correspond to killed, and curved ones to alive individuals.

The cells of the Streptomyces strains alone did not affect significantly the survival of nematodes in tests made on solid medium, while the two strains of the pathogenic Salmonella caused mortality. However, supernatants from cell-free cultures of S. melanosporofaciens AGL225 and S. yatensis AGL148 had a strong nematicidal effect (FIG. 5, TABLE 4). It was noted that also at high doses, a part of the nematode individuals were lysed and practically unrecognizable. This effect was attributed to the possible action of chitinases, and the numerous nematotoxic metabolites produced by the Streptomyces strains. Such property can be considered important for the use of the strains as biological nematicides, with applications in plant protection.

TABLE 4

Nematicidal activity of S. melanosporofaciens AGL225 and S. yatensis AGL148.

| Treatment | Dilution | Initial | Dead | Alive | Lysed |
|---|---|---|---|---|---|
| Supernatant AGL148 | 1/2 | 58 | 11 | 0 | 47 |
|  | 1/10 | 55 | 21 | 0 | 34 |
| Supernatant AGL225 | 1/2 | 62 | 36 | 0 | 26 |
|  | 1/10 | 65 | 45 | 0 | 20 |
| Sodium azide (kill control) | 1 | 70 | 68 | 0 | 2 |
| Control medium ISP2 | 1 | 60 | 0 | 57 | 3 |
| Control buffer M9 | 1 | 61 | 0 | 60 | 1 |

Example 7. Effectiveness of the Strains of the Invention in the Control of Bacterial and Fungal Infections in Plants To demonstrate the effectiveness of the strains of the invention, several tests were performed in controlled environment conditions (greenhouse) on several representative pathosystems (crop plants and pathogen), involving both plant pathogenic bacteria and phytopathogenic fungi. The bacterial pathosystems were X. arboricola pv. pruni (Xap) in GF677 an almond×peach hybrid rootstock, P. syringae pv. tomato (Pto) in tomato, and E. amylovora on pear. In the case of the fungi pathosystems S. sclerotiorum on lettuce, B. cinerea in tomato, and F. oxysporum f. sp. radicis lycopersici (Forl) in tomato, were used. Results are shown in FIG. 6.

For the preparation of the treatments, the strains of Streptomyces were seeded in ISP2 and incubated at 28° C. for five days, to obtain vegetative cells, spores and fermentation metabolites. Suspensions of the strains in sterile distilled water were prepared as described above in Example 2. Viable counts were 3-4×10$^{*8}$ cfu/ml, depending on the assay.

a) Control of Xanthomonas arboricola pv. Pruni in Prunus GF667 Prunus rootstock plants, an almond and peach hybrid (Prunus amygdalus×Prunus persica) were used, when presented between 6 to 7 leaves. The experimental design consisted of 3 repetitions of 3 plants per repetition for each treatment. Treatments with strains of Streptomyces were applied with an airbrush until the drop point, 7 and 1 day before inoculation of the pathogen. S. saraceticus SS31 was used as reference control. The strain of X. arboricola pv. pruni CFBP 5563, the pathogen, was inoculated onto the surface of LB agar plates and incubated at 28° C., and the inoculum was prepared from plates incubated for 24 h. The suspension of the pathogen was adjusted to a concentration of approximately 6.8×10$^{*7}$ cfu/ml. All leaves within a plant were inoculated by spraying with an airbrush until the run-off point. Once inoculated, the plants were placed in plastic bags for 48 h to accelerate the process of infection, and then incubated at 26±2° C. with a relative humidity of 60% and 16 h of light during the day and 15±2° C., 80% RH and 8 h dark overnight. Assessments were made at 15 days post-inoculation of pathogen (dpi) assigning a disease index based on the leaf area affected. 0: no symptoms; 1, 0 to 25% of the leaf area; 2, 25-50% of the leaf area, 3, 50 to 75% of the leaf area; and 4, over 75%.

Figure 6:
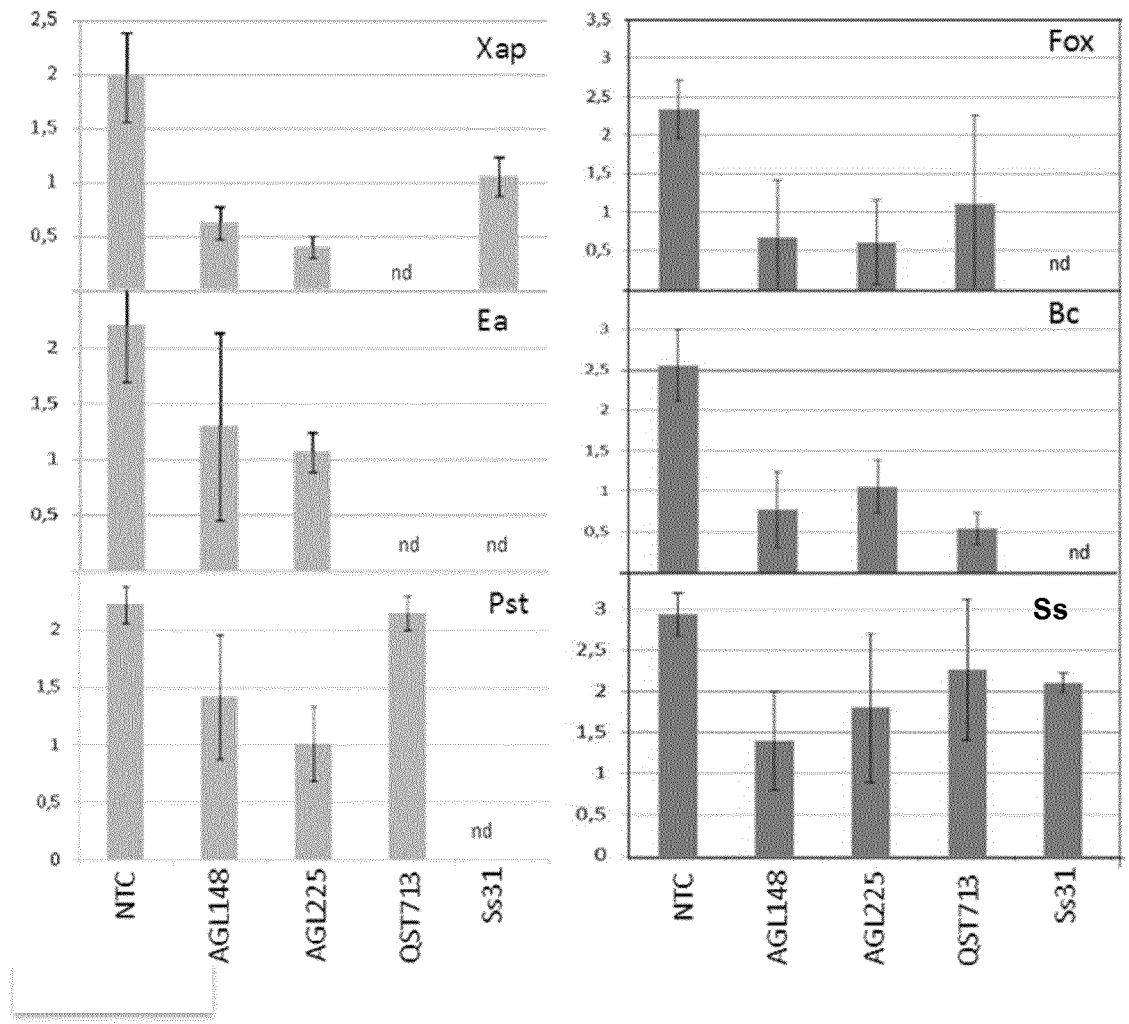
FIG. 6. Effect of treatment with the strains *Streptomyces* AGL225 and AGL148 in controlling infections caused by *X. arboricola* pv. pruni in the *Prunus* hybrid peach×almond GF677 (Xap), *E. amylovora* on pear (Ea), *P. syringae* pv. tomato in tomato (Pst), *F. oxysporum* f.sp. *lycopersici* in tomato (Fox), *Botrytis cinerea* in tomato (Bc), and *S. sclerotiorum* on lettuce (Ss). The results are compared with an untreated (NTC) control. The Y axis represents disease severity. X axis represents the strain code. QST713 (*Bacillus subtilis*) and Ss31 (*Streptomyces saraceticus*) strains were used as reference biocontrol. Values are means of three replicates and error bars represent 95% confidence interval of the mean. Nd: not determined.

FIG. 6 (Xap) shows the effect of treatments with S. saraceticus SS31 as a reference control, as well as with the strains of Streptomyces of the invention. AGL148 and AGL225 strains were effective and significantly reduced the severity of infection relative to non-treated control.

b) Control of *Erwinia amylovora* on Pear

This test was conducted with 2 years old pear plants of cultivar Conference (CAV clone) self-rooted and grown in pots. The experimental design consisted of three repetitions of 3 plants per repetition, for each treatment. In this test treatments were applied at 7 and 1 days before pathogen inoculation. Treatments with strains were performed in the upper younger leaves (3-4 leaves/plant) with an airbrush to the drop point. At one day before treatment the plants were wounded with an incision in the main nerve of the leaves. Treatments consisted of the strains of *Streptomyces*. The pathogen strain used was *E. amylovora* EPS101 which was thawed and maintained by subculturing in fresh LB agar plates incubated at 28° C. A fresh inoculum was prepared for infections at a dose of $3.5 \times 10^7$ cfu/ml. Inoculation of *E. amylovora* was performed by applying a drop of 10 ul into each wound. Once Inoculated, the plants were placed into plastic bags to accelerate the process of infection and keep the pathogen in quarantine. The assessment of disease was performed at 5, 7 and 12 dpi, using an index from 0 to 4 based on the development of necrosis in the plant: 0: no infection 1: onset of necrosis out the wound; 2: onset of necrosis by leaf nerve; 3: necrosis reaches the petiole, and 4: necrosis from leaf to shoot. FIG. 6 (Ea) shows as strain AGL225 significantly reduced levels of infection compared with the untreated control.

c) Control of *Pseudomonas syringae* pv. Tomato in Tomato Plants

To obtain tomato plants, seeds of the variety Rio Grande were shown in alveoli and 15-21 days after were transplanted to pots. The conditions in the greenhouse were 16 h light at 25±2° C. and 8 h dark at 15±2° C. The experimental design consisted of 3 repetitions of 3 plants per repetition, per each treatment. *P. syringae* pv. tomato (Pst) DC3000 strain was used as pathogen. For inoculum preparation a colony was thawed and maintained in fresh LB plates incubated at 28 for 24 h. A water suspension was prepared and was adjusted to approximately $10^{*8}$ cfu/ml. The inoculum was complemented with diatomaceous earth (1 g/L) to facilitate microwounds in the leaves and therefore the infection. Each plant was inoculated with the airbrush until drop point, was incubated at 25±2° C. with relative humidity of 60% and 16 h of light during the day and 15±2° C., 80% RH and 8 h of darkness during the night.

The treatments started when the third and fourth true leaves, emerged and were made at 7 and 1 day before the pathogen inoculation. *Bacillus subtilis* QST713 was used as control. Assessments were made at 7 dpi and were rated depending on the affected leaf area, according to an index of 0 when no symptoms are detected; 1, less than 25% of area affected, 25-50% leaf area 2 affected; 3, 50-75% of the leaf area affected and 4, over 75% of affected area. All treatments except Serenade showed a reduction in the severity of infection by Pst (FIG. 6 Pst). AGL225 and AGL148 strains were effective in the reduction of the severity of the disease, compared with non-treated control.

d) Control of *Fusarium oxysporum* f. Sp. *radicis lycopersici* in Tomato

Tomato plants were prepared as in Example 7 paragraph b. For pathogen inoculum preparation *F. oxysporum* f. sp. *radicis lycopersici*, the FORL strain was used. PDA agar plates were seeded 10 days prior to inoculation of the pathogen, and were incubated at 23-25° C. with a photoperiod of 16 h light and 8 h dark. A suspension of the pathogen was prepared and adjusted to $2.9 \times 10^{*6}$ conidia/mL. Before inoculating the fungus, four lesions were made on the roots of the plant using a scalpel. Each plant was inoculated with 10 ml of the suspension of FORL by irrigation. The first treatments performed started when the third and fourth true leaves in plants emerged. Treatments were performed at 7 and 1 before pathogen inoculation and 20 ml of each strain preparation were applied by watering. *Bacillus subtilis* QST713 was used as control. Assessments of diseased plants were made at 21 dpi. An index was used based on the evolution of necrosis in the stem: 0: no infection; 1 lesion surface is not reaching the stem; 2: infection rises through the stem of the plant, and 3: the plant was dead. As shown in FIG. 6 (Fox), AGL148 and AGL225 strains were effective in controlling infections.

e) Control of *Botrytis cinerea* on Tomato

Tomato plants were prepared as in Example 7 paragraph c. For pathogen inoculum preparation a *B. cinerea* strain was used. PDA agar plates were seeded 10 days prior to inoculation of the pathogen, and were incubated at 23-25° C. with a photoperiod of 16 h light and 8 h dark. A suspension of the pathogen was prepared and adjusted to $2.9 \times 10^6$ conidia/mL. As reference treatments, Serenade MAX (*Bacillus subtilis* QST713), a commercial product, was used as control. Plants were sprayed with the fungal suspension until runoff point. Assessments were done at 7 days after pathogen inoculation (dpi). A severity index in leaves was established as 0, non infected; 1, less than 25% surface; 2, 25 to less than 50%; 3, 50 to less than 75%; 4, more than 75%. FIG. 6 (Bc) shows that strains AGL148 and AGL225 were highly effective, as well as *B. subtilis* QST713.

f) Control of *Sclerotinia sclerotiorum* on Lettuce

Lettuce seeds were shown in alveoli and 15-21 days after were transplanted to pots. The treatments were performed at 7 and 1 day before inoculation of the pathogen. As reference treatments, Serenade MAX (*Bacillus subtilis* QST713) and *S. saraceticus* SS31 were used as controls. The phytopathogenic fungus *S. sclerotiorum* was cultured in 250 ml Erlenmeyer flasks with 25 g of autoclaved rye seed and 25 ml of distilled water. Inoculation of the pathogen to the plants was performed 21 days after sowing and each plant was infected with one infested seed rye. Assessments were done at 3 and 7 days after pathogen inoculation (dpi). A severity index was established as 0: a healthy plant; 1: root rot to the crown; 2: rot affects crown; 3: the rot exceeds the crown, and 4: dead lettuce. FIG. 6 (Ss) shows that the severity of the disease in the non-treated controls was quite high. Strains AGL148 and AGL225 had an inhibitory effect.

CITATION LIST

Aimé. S.; Cordier, C.; Alabouvette, C.; Olivain, c. 2008. Comparative analysis of PR gene expression in tomato Inoculated With virulent *Fusarium oxysporum* f. sp. *lycopersici* and *F. oxysporum* Fo47 the biocontrol strain. *Physiol Mol Plant Pathol.* 73 (1-3): 9-15. doi: 10.1016/j.pmpp.2008.10.001.

Ait-Barka E. et al. 31 Mar. 2009. Use of composition comprising at least one actynomicetes strains for control of miro organimsms inducing plant disease, where actinomycetes strains are different from *Streptomyces melanosporofaciens*. WO2010115802-A1.

Beaulieu C. et al. 8 Dec. 2003. Geldamycin-producing strains, uses thereof and methods of producing same. US2007/0237755-A1.

Bervanakis, G. 2008. Detection and Expression of Biosynthetic Genes in Actinobacteria. Thesis for the degree of Master of Science. Flinders University.

Bonaterra, A.; Camps, J.; Montesinos, E. 2005. Osmotically induced trehalose and glycine betaine accumulation improves tolerance to desiccation, survival and efficacy of the postharvest biocontrol agent *Pantoea agglomerans* EPS125. FEMS Microbiology Letters. 250:7-15.

Boroujeni, M E; Das, A.; Prashanthi, K.; Suryan, S. and Bhattacharya, S. 2012. Enzymatic screening and random amplified polymorphic DNA fingerprinting of soil streptomyces isolated from Wayanad district in Keralda, India. Journal of Biological Sciences 12 (1): 43-50.

Cabrefiga, J., Francés, J., Montesinos, E., Bonaterra, A. 2011. Improvement of fitness and efficacy of a fire blight biocontrol agent via nutritional enhancement combined with osmoadaptation. Applied and Environmental Microbiology 77: 3174-3181.

Cabrefiga, J., Francés, J, Montesinos, E., Bonaterra, A. 2014. Improvement of a dry formulation of *Pseudomonas fluorescens* EPS62e for fire blight disease biocontrol by combination of culture osmoadaptation with a freeze-drying lyoprotectant. J. Applied Microbiology. June 2014; DOI: 10.1111/jam.12582.

Dahllöf, I.; Baillie, H.; Kjelleberg, S. 2000. rpoB-based microbial community analysis 16S rRNA Avoids limitations inherent in intraspecies gene heterogeneity. *Appl Environ Microbiol* 66: 3376-3380.

Frändberg, E.; Schnürer, J. 1998. Antifungal activity of chitinolytic bacteria isolated from cereal grain stored airtight. 127: 121-127.

Freeman, B C; and Beattie, G A 2008. An Overview of Plant Defenses Against Pathogens and Herbivores. The Plant Health instructor. DOI: 10.1094/PHI-I-2008-0226-01.

Gharaibeh, R.; Saadoun, I.; Mahasneh, A. 2003. Genotypic and phenotypic Characteristics of antibiotic-producing Streptomyces soil Investigated by RAPD. *J Basic Microbiol.* 43 (1): 18-27. doi: 10.1002/jobm.200390000.

Kim, B J; Kim, C J; Chun, J.; Koh, Y H; Lee, S H; Hyun, J W; Cha, C Y; Kook, 2004. Phylogenetic analysis of the generated YH Streptomyces and Kitasatospora based on partial RNA polymerase β-subunit gene (rpoB) sequences. *Int J Syst Evol Microbiol* 54 (2): 593-598. doi: 10.1099/ijs.0.02941-0.

Kong, L.; Tzeng, D.; Yang, C. 0.2001. Generation of PCR-based DNA Fragments for Specific Detection of *Streptomyces saraceticus* N45. Proc. Natl. Sci. 25 (2): 119-127.

Kuchma, A J; Roberts, M A; Knaebel, D B and Crawford, D L 1998.—Small-scale isolation of genomic DNA from *Streptomyces* mycelia or spores. BioTechniques 24: 452-457.

Montesinos, E. and Bonaterra A. 2009. Microbial pesticides. Encyclopedia of Microbiology, Publisher: Elsevier Inc., Editors: Schaechter M, pp. 110-120.

Parente, E.; Brienza, C.; Moles, M.; Riccardi, A. 1995. A comparison of methods for the measurement of bacteriocin activity. Journal of Microbiological Methods, 22: 95-108).

Rintala, H.; Nevalainen, A.; Rönkä, E.; Suutari, M. 2001. PCR primers targeting the 16S rRNA gene for the specific detection of streptomycetes. *Mol Cell Probes.* 15 (6): 337-347. doi: 10.1006/mcpr.2001.0379.

Rodriguez-Kabana, R.; Godoy G, Shelby R A. 1983. The determination of soil chitinase activity: Conditions for assay and ecological studies. Plant Soil. 106: 95-106.

Sambrook, J. and Russell, D W "Molecular Cloning: A Laboratory Manual", Chapter 13, "Mutagenesis", Cold Spring Harbor, 3rd Ed., 2001.

Shepherd, M D; Kharel, M K; Bosserman, M A; Rohr, J. 2010. Laboratory maintenance of *Streptomyces* species. *Curr Protoc Microbiol; Chapter* 1: 1-10. doi: 10.1002/9780471729259. mc10e01s18.Laboratory.

Shirling, E B and Gottlieb D. 1966. Methods for characterization of *Streptomyces* species. International Journal of Systematic Bacteriology. 13: 313-340.

Tamura K, Stecher G, Peterson D, Filipski A, and Kumar S (2013) Molecular Evolutionary Genetics Analysis Version 6.0 program, Molecular Biology and Evolution 30: 2725-2729.

Tzeng D. et al. 10 May 2005. Biocontrol formulation containing *Streptomyces* spp., method for preparing the formulation and relevant use. US20140057336 Al.

Williams, J G K; Kubelik, A R; Livak, K L; Rafalski, J A; S V Tingey 1990. DNA polymorphisms amplified by arbitrary primers are useful as genetic markers", Nucleic Acids Res., 1990, vol. 18, pp. 6531-6535).

Yoon-Byung D. et al. A novel *Streptomyces yatensis* CJS-24 KCTC 11107BP active against plant fungal pathogens and a microbial pesticide using the same. KR100869668.

---

The invention claimed is:

1. A method for obtaining viable cells of *Streptomyces melanosporofaciens* strain AGL225 identified in the Spanish Type Culture Collection (CECT) as *Streptomyces melanosporofaciens* CECT9420 comprising the steps of:
   (i) inoculating the AGL225 strain in a suitable culture medium,
   (ii) subjecting the inoculated culture medium of step (i) to conditions suitable for the growth of the strain to yield a cell suspension, the conditions comprising a temperature from 25 to 30° C., pH from 6 to 8, and oxygen concentration from 10 to 50%,
   (iii) subjecting the cell suspension of step (ii) to separation to yield viable cells of *Streptomyces melanosporofaciens* AGL225 and a metabolite-containing supernatant,
   (iv) collecting the cells of *Streptomyces melanosporofaciens* AGL225.

2. The method according to claim 1, further comprising subjecting the obtained cells to a dehydration process.

3. The method according to claim 1, further comprising resuspending the cells to a desired density.

4. A *Streptomyces melanosporofaciens* AGL225 metabolite-containing supernatant obtainable by a method comprising:
   (a) steps (i)-(iii) as defined in claim 1; and
   (b) collecting the supernatant and, optionally, subjecting the supernatant to a concentration process.

5. A composition comprising the *Streptomyces melanosporofaciens* AGL225 metabolite-containing supernatant as defined in claim 4 and one or more agriculturally acceptable compounds selected from the group consisting of plant strengtheners, nutrients, wetting agents, compounds that improve adherence, buffering compounds, stabilizers, antioxidants, osmoprotectants and sun protectants.

6. The composition according to claim 5, that comprises at least one osmoprotectant.

7. A method for the biological control of plant pests comprising administering to a plant, the *Streptomyces melanosporofaciens* AGL225 metabolite-containing supernatant as defined in claim 4.

8. The method according to claim 7 that comprises administering the *Streptomyces melanosporofaciens* AGL225 metabolite-containing supernatant and one or more agriculturally acceptable compounds selected from the group consisting of plant strengtheners, nutrients, wetting agents, compounds that improve adherence, buffering compounds, stabilizers, antioxidants, osmoprotectants and sun protectants.

9. A composition comprising *Streptomyces melanosporofaciens* strain AGL225 identified in the Spanish Type Culture Collection (CECT) as *Streptomyces melanosporofaciens* CECT9420 and one or more agriculturally acceptable compounds selected from the group consisting of plant strengtheners, nutrients, wetting agents, compounds that improve adherence, buffering compounds, stabilizers, antioxidants, osmoprotectants and sun protectants.

10. The composition according to claim 9, that comprises at least one osmoprotectant.

11. The composition according to claim 9, further comprising an additional pesticide.

12. The composition according to claim 11, wherein the additional pesticide is another bacterial strain with fungicidal, bactericidal and/or nematicidal activity.

13. The composition according to claim 12, wherein the other bacterial strain is *Streptomyces yatensis* AGL148 strain identified in the Spanish Type Culture Collection as *Streptomyces yatensis* CECT9421.

14. A method for the biological control of plant pests comprising administering to a plant, *Streptomyces melanosporofaciens* strain AGL225 identified in the Spanish Type Culture Collection (CECT) as *Streptomyces melanosporofaciens* CECT9420.

15. The method according to claim 14 that comprises administering the *Streptomyces melanosporofaciens* AGL225 in the form of a composition comprising *Streptomyces melanosporofaciens* AGL225 and one or more agriculturally acceptable compounds selected from the group consisting of plant strengtheners, nutrients, wetting agents, compounds that improve adherence, buffering compounds, stabilizers, antioxidants, osmoprotectants and sun protectants.

16. The method according to claim 15, wherein the composition comprises at least one osmoprotectant.

17. The method according to claim 15, wherein the composition further comprises an additional pesticide.

18. The method according to claim 17, wherein the pesticide is another bacterial strain with fungicidal, bactericidal and/or nematicidal activity.

19. The method according to claim 18, wherein the other bacterial strain is *Streptomyces yatensis* AGL148 strain identified in the Spanish Type Culture Collection as *Streptomyces yatensis* CECT9421.

20. The method according to claim 14, wherein the plant pests are fungi, bacteria, or nematodes.

* * * * *

SEQUENCE LISTING

```
<160> NUMBER OF SEQ ID NOS: 39

<210> SEQ ID NO 1
<211> LENGTH: 20
<212> TYPE: DNA
<213> ORGANISM: Artificial Sequence
<220> FEATURE:
<223> OTHER INFORMATION: StrepB primer

<400> SEQUENCE: 1
acaagccctg gaaacggggt                                               20

<210> SEQ ID NO 2
<211> LENGTH: 19
<212> TYPE: DNA
<213> ORGANISM: Artificial Sequence
<220> FEATURE:
<223> OTHER INFORMATION: StrepF primer

<400> SEQUENCE: 2
acgtgtgcag cccaagaca                                                19
```

<210> SEQ ID NO 3
<211> LENGTH: 18
<212> TYPE: DNA
<213> ORGANISM: Artificial Sequence
<220> FEATURE:
<223> OTHER INFORMATION: StrepE primer

<400> SEQUENCE: 3
caccaggaat tccgatct                                                     18

<210> SEQ ID NO 4
<211> LENGTH: 20
<212> TYPE: DNA
<213> ORGANISM: Artificial Sequence
<220> FEATURE:
<223> OTHER INFORMATION: SRPOF1 primer for 16S

<400> SEQUENCE: 4
tcgaccactt cggcaaccgc                                                   20

<210> SEQ ID NO 5
<211> LENGTH: 20
<212> TYPE: DNA
<213> ORGANISM: Artificial Sequence
<220> FEATURE:
<223> OTHER INFORMATION: SRPOR1 primer for 16S

<400> SEQUENCE: 5
tcgatcgggc acatgcggcc                                                   20

<210> SEQ ID NO 6
<211> LENGTH: 10
<212> TYPE: DNA
<213> ORGANISM: Artificial Sequence
<220> FEATURE:
<223> OTHER INFORMATION: LIT primer for RAPD

<400> SEQUENCE: 6
tgccgagctg                                                              10

<210> SEQ ID NO 7
<211> LENGTH: 10
<212> TYPE: DNA
<213> ORGANISM: Artificial Sequence
<220> FEATURE:
<223> OTHER INFORMATION: OPA9 primer for RAPD

<400> SEQUENCE: 7
gggtaacgcc                                                              10

<210> SEQ ID NO 8
<211> LENGTH: 24
<212> TYPE: DNA
<213> ORGANISM: Artificial Sequence
<220> FEATURE:
<223> OTHER INFORMATION: OPA10 primer for RAPD

<400> SEQUENCE: 8
gttggcgggt gtcggggctg gctt                                              24

<210> SEQ ID NO 9
<211> LENGTH: 10
<212> TYPE: DNA
<213> ORGANISM: Artificial Sequence
<220> FEATURE:

<223> OTHER INFORMATION: OPA2 primer for RAPD

<400> SEQUENCE: 9
gtgatcgcag                                                                    10

<210> SEQ ID NO 10
<211> LENGTH: 10
<212> TYPE: DNA
<213> ORGANISM: Artificial Sequence
<220> FEATURE:
<223> OTHER INFORMATION: OPA B9 primer for RAPD

<400> SEQUENCE: 10
gggcgactac                                                                    10

<210> SEQ ID NO 11
<211> LENGTH: 21
<212> TYPE: DNA
<213> ORGANISM: Artificial Sequence
<220> FEATURE:
<223> OTHER INFORMATION: d8635 primer for RAPD

<400> SEQUENCE: 11
gagcggccaa agggagcaga c                                                       21

<210> SEQ ID NO 12
<211> LENGTH: 10
<212> TYPE: DNA
<213> ORGANISM: Artificial Sequence
<220> FEATURE:
<223> OTHER INFORMATION: 1.80.5 primer for RAPD

<400> SEQUENCE: 12
accccagccg                                                                    10

<210> SEQ ID NO 13
<211> LENGTH: 10
<212> TYPE: DNA
<213> ORGANISM: Artificial Sequence
<220> FEATURE:
<223> OTHER INFORMATION: 1.80.7 primer for RAPD

<400> SEQUENCE: 13
gcacgccgga                                                                    10

<210> SEQ ID NO 14
<211> LENGTH: 10
<212> TYPE: DNA
<213> ORGANISM: Artificial Sequence
<220> FEATURE:
<223> OTHER INFORMATION: 2.80.11 primer for RAPD

<400> SEQUENCE: 14
gcagcagccg                                                                    10

<210> SEQ ID NO 15
<211> LENGTH: 10
<212> TYPE: DNA
<213> ORGANISM: Artificial Sequence
<220> FEATURE:
<223> OTHER INFORMATION: 4.80.35 primer for RAPD

<400> SEQUENCE: 15
cacctgccgc                                                                    10

```
<210> SEQ ID NO 16
<211> LENGTH: 10
<212> TYPE: DNA
<213> ORGANISM: Artificial Sequence
<220> FEATURE:
<223> OTHER INFORMATION: 4.80.36 primer for RAPD

<400> SEQUENCE: 16
ggcctccacg                                                          10

<210> SEQ ID NO 17
<211> LENGTH: 10
<212> TYPE: DNA
<213> ORGANISM: Artificial Sequence
<220> FEATURE:
<223> OTHER INFORMATION: 4.80.37 primer for RAPD

<400> SEQUENCE: 17
cgccaggagc                                                          10

<210> SEQ ID NO 18
<211> LENGTH: 20
<212> TYPE: DNA
<213> ORGANISM: Artificial Sequence
<220> FEATURE:
<223> OTHER INFORMATION: Actin F

<400> SEQUENCE: 18
cactgtatgc cagtggtcgt                                               20

<210> SEQ ID NO 19
<211> LENGTH: 20
<212> TYPE: DNA
<213> ORGANISM: Artificial Sequence
<220> FEATURE:
<223> OTHER INFORMATION: Actin R

<400> SEQUENCE: 19
gacggagaat ggcatgtgga                                               20

<210> SEQ ID NO 20
<211> LENGTH: 20
<212> TYPE: DNA
<213> ORGANISM: Artificial Sequence
<220> FEATURE:
<223> OTHER INFORMATION: PR1a F

<400> SEQUENCE: 20
tcttgtgagg cccaaaattc                                               20

<210> SEQ ID NO 21
<211> LENGTH: 20
<212> TYPE: DNA
<213> ORGANISM: Artificial Sequence
<220> FEATURE:
<223> OTHER INFORMATION: PR1a R

<400> SEQUENCE: 21
atagtctggc ctctcggaca                                               20

<210> SEQ ID NO 22
<211> LENGTH: 20
<212> TYPE: DNA
<213> ORGANISM: Artificial Sequence
<220> FEATURE:
<223> OTHER INFORMATION: GluA F
```

```
<400> SEQUENCE: 22
tcttgtgagg cccaaaattc                                              20

<210> SEQ ID NO 23
<211> LENGTH: 20
<212> TYPE: DNA
<213> ORGANISM: Artificial Sequence
<220> FEATURE:
<223> OTHER INFORMATION: GluA R

<400> SEQUENCE: 23
atagtctggc ctctcggaca                                              20

<210> SEQ ID NO 24
<211> LENGTH: 21
<212> TYPE: DNA
<213> ORGANISM: Artificial Sequence
<220> FEATURE:
<223> OTHER INFORMATION: GLUB F

<400> SEQUENCE: 24
ttgtcgccac caacattcac a                                            21

<210> SEQ ID NO 25
<211> LENGTH: 20
<212> TYPE: DNA
<213> ORGANISM: Artificial Sequence
<220> FEATURE:
<223> OTHER INFORMATION: GLUB R

<400> SEQUENCE: 25
accatctcgc gtgttccatc                                              20

<210> SEQ ID NO 26
<211> LENGTH: 20
<212> TYPE: DNA
<213> ORGANISM: Artificial Sequence
<220> FEATURE:
<223> OTHER INFORMATION: chia F

<400> SEQUENCE: 26
ttcggcactg atggaagtgg                                              20

<210> SEQ ID NO 27
<211> LENGTH: 21
<212> TYPE: DNA
<213> ORGANISM: Artificial Sequence
<220> FEATURE:
<223> OTHER INFORMATION: chia R

<400> SEQUENCE: 27
ttttaagctt gctacacgcg g                                            21

<210> SEQ ID NO 28
<211> LENGTH: 20
<212> TYPE: DNA
<213> ORGANISM: Artificial Sequence
<220> FEATURE:
<223> OTHER INFORMATION: PERAJ F

<400> SEQUENCE: 28
aggcccattt tatccggtgg                                              20

<210> SEQ ID NO 29
<211> LENGTH: 20
```

```
<212> TYPE: DNA
<213> ORGANISM: Artificial Sequence
<220> FEATURE:
<223> OTHER INFORMATION: PERAJ R

<400> SEQUENCE: 29
gctaaggcca cgtctagcaa                                              20

<210> SEQ ID NO 30
<211> LENGTH: 20
<212> TYPE: DNA
<213> ORGANISM: Artificial Sequence
<220> FEATURE:
<223> OTHER INFORMATION: PER1 F

<400> SEQUENCE: 30
tcttagctgt tgcagctcgt                                              20

<210> SEQ ID NO 31
<211> LENGTH: 20
<212> TYPE: DNA
<213> ORGANISM: Artificial Sequence
<220> FEATURE:
<223> OTHER INFORMATION: PER1 R

<400> SEQUENCE: 31
ctagtgtatg gccaccggac                                              20

<210> SEQ ID NO 32
<211> LENGTH: 20
<212> TYPE: DNA
<213> ORGANISM: Artificial Sequence
<220> FEATURE:
<223> OTHER INFORMATION: HARP F

<400> SEQUENCE: 32
attatggccc gtccattccg                                              20

<210> SEQ ID NO 33
<211> LENGTH: 20
<212> TYPE: DNA
<213> ORGANISM: Artificial Sequence
<220> FEATURE:
<223> OTHER INFORMATION: HARP R

<400> SEQUENCE: 33
atgcaatgac tccgaggacg                                              20

<210> SEQ ID NO 34
<211> LENGTH: 24
<212> TYPE: DNA
<213> ORGANISM: Artificial Sequence
<220> FEATURE:
<223> OTHER INFORMATION: strD01f

<400> SEQUENCE: 34
cttcgccatg tatctcggcg acaa                                         24

<210> SEQ ID NO 35
<211> LENGTH: 20
<212> TYPE: DNA
<213> ORGANISM: Artificial Sequence
<220> FEATURE:
<223> OTHER INFORMATION: strD01r

<400> SEQUENCE: 35
```

-continued

```
tgccggtgtc cttccagtag                                                    20

<210> SEQ ID NO 36
<211> LENGTH: 19
<212> TYPE: DNA
<213> ORGANISM: Artificial Sequence
<220> FEATURE:
<223> OTHER INFORMATION: act04f

<400> SEQUENCE: 36
gatggtctcc accggctgc                                                     19

<210> SEQ ID NO 37
<211> LENGTH: 21
<212> TYPE: DNA
<213> ORGANISM: Artificial Sequence
<220> FEATURE:
<223> OTHER INFORMATION: act06r

<400> SEQUENCE: 37
gtctcgtggc ggtcgttctg c                                                  21

<210> SEQ ID NO 38
<211> LENGTH: 23
<212> TYPE: DNA
<213> ORGANISM: Artificial Sequence
<220> FEATURE:
<223> OTHER INFORMATION: pcb03f

<400> SEQUENCE: 38
cgagtcctgg tgctacctga acc                                                23

<210> SEQ ID NO 39
<211> LENGTH: 22
<212> TYPE: DNA
<213> ORGANISM: Artificial Sequence
<220> FEATURE:
<223> OTHER INFORMATION: pcb03r

<400> SEQUENCE: 39
tcatcgacac gtccaggtgg tc                                                 22
```